United States Patent
Aoki et al.

(10) Patent No.: US 11,134,840 B2
(45) Date of Patent: Oct. 5, 2021

(54) OPHTHALMOLOGICAL DEVICE, OPHTHALMOLOGICAL IMAGE PROCESSING METHOD, AND STORAGE MEDIUM

(71) Applicant: TOPCON CORPORATION, Tokyo (JP)

(72) Inventors: Hiroyuki Aoki, Saitama (JP); Taiki Aimi, Musashino (JP)

(73) Assignee: TOPCON CORPORATION, Tokyo (JP)

( * ) Notice: Subject to any disclaimer, the term of this patent is extended or adjusted under 35 U.S.C. 154(b) by 54 days.

(21) Appl. No.: 16/625,277

(22) PCT Filed: May 17, 2018

(86) PCT No.: PCT/JP2018/019068
§ 371 (c)(1),
(2) Date: Dec. 20, 2019

(87) PCT Pub. No.: WO2018/235471
PCT Pub. Date: Dec. 27, 2018

(65) Prior Publication Data
US 2020/0214556 A1  Jul. 9, 2020

(30) Foreign Application Priority Data

Jun. 21, 2017 (JP) .............................. JP2017-120944

(51) Int. Cl.
*A61B 3/10* (2006.01)
*G06T 7/73* (2017.01)
(Continued)

(52) U.S. Cl.
CPC ............ *A61B 3/102* (2013.01); *A61B 3/1241* (2013.01); *G06K 9/4604* (2013.01);
(Continued)

(58) Field of Classification Search
CPC ..................... G06T 7/73; G06T 7/0012; G06T 2207/10101; G06T 2207/30041;
(Continued)

(56) References Cited

U.S. PATENT DOCUMENTS 8,879,813 B1 * 11/2014 Solanki .................... A61B 3/14
382/128
2010/0149183 A1 * 6/2010 Loewke .................... G06K 9/32
345/424
(Continued)

FOREIGN PATENT DOCUMENTS

| JP | 2002-058647 A | 2/2002 |
| JP | 2016-198447 A | 12/2016 |
| JP | 2016-209200 A | 12/2016 |

OTHER PUBLICATIONS

International Search Report and Written Opinion dated Aug. 7, 2018 for PCT/JP2018/019068 filed on May 17, 2018, 7 pages including English Translation of the International Search Report.
(Continued)

Primary Examiner — Jon Chang
(74) Attorney, Agent, or Firm — Xsensus LLP

(57) ABSTRACT

An ophthalmological device of some embodiment examples includes a memory, detecting processor, identifying processor, transforming processor, and composing processor. The memory stores a plurality of angiograms acquired by applying optical coherence tomography to an eye fundus. The detecting processor is configured to detect a feature point from each of the angiograms. The identifying processor is configured to identify a plurality of feature point groups from among a plurality of feature points detected from the angiograms. Each feature point group corresponds to a same site of the eye fundus. The transforming processor is configured to transform at least part of the angiograms based on the feature point groups. The composing processor is con-
(Continued)

figured to compose two or more angiograms of the angiograms at least part of which has been transformed, based on the feature point groups.

11 Claims, 14 Drawing Sheets

(51) Int. Cl.
  *A61B 3/12* (2006.01)
  *G06K 9/46* (2006.01)
  *G06K 9/62* (2006.01)
  *G06T 7/00* (2017.01)
(52) U.S. Cl.
  CPC .......... *G06K 9/6232* (2013.01); *G06T 7/0012* (2013.01); *G06T 7/73* (2017.01); *G06T 2200/32* (2013.01); *G06T 2207/10101* (2013.01); *G06T 2207/30041* (2013.01); *G06T 2211/404* (2013.01)
(58) Field of Classification Search
  CPC ............ G06T 2211/404; G06T 3/4038; G06K 9/4604; G06K 9/6232; A61B 3/102; A61B 3/1241; A61B 3/10
  See application file for complete search history.

(56) References Cited

U.S. PATENT DOCUMENTS

2016/0317016 A1   11/2016   Oishi et al.
2017/0316565 A1*  11/2017   Leahy ...................... A61B 3/12
2018/0116501 A1    5/2018   Akiba et al.

OTHER PUBLICATIONS

Schwartz, D. M., et al., "Phase-Variance Optical Coherence Tomography: A Technique for Noninvasive Angiography," Journal of American Academy of Ophthalmology, Ophthalmology, vol. 121, No. 1, Elsevier Inc., Jan. 2014, pp. 180-187.

Extended European search report dated Feb. 12, 2021, in corresponding European patent Application No. 18821483.7, 9 pages.

Wei et al., "The Retinal Image Mosaic Based on Invariant Feature and Hierarchial Transformation Models", 2009, IEEE, total 5 pages.

Wang et al., "Automatic Fundus Images Mosaic Based on SIFT Feature", 2010 3rd International Congress on Image and Signal Processing (CISP2010), 2010, IEEE, pp. 2747-2751.

Li et al., "A Robust Feature-Based Method for Mosaic of the Curved Human Color Retinal Images", 2008 International Conference on BioMedical Engineering and Informatics, vol. 1, 2008, IEEE, pp. 845-849.

Adel et al., "Image Stitching based on Feature Extraction Techniques: A Survey", International Journal of Computer Applications (0975-8887), vol. 99, No. 6, Aug. 2014, total 8 pages.

Kale et al., "A Technical Analysis of Image Stitching Algorithm," International Journal of Computer Science and Information Technologies, vol. 6 (1), 2015, pp. 284-288.

Müller et al., "Robust image registration for fusion" Information Fusion, Elsevier, ScienceDirect, vol. 8, 2007, pp. 347-353.

Zhang et al., "A Fast Strategy for Image Matching Using Hausdorff Distance", Proceedings of the 2003 IEEE International Conference on Robotics, Intelligent Systems and Signal Processing, Oct. 2003, pp. 915-919, Changsha, China.

* cited by examiner

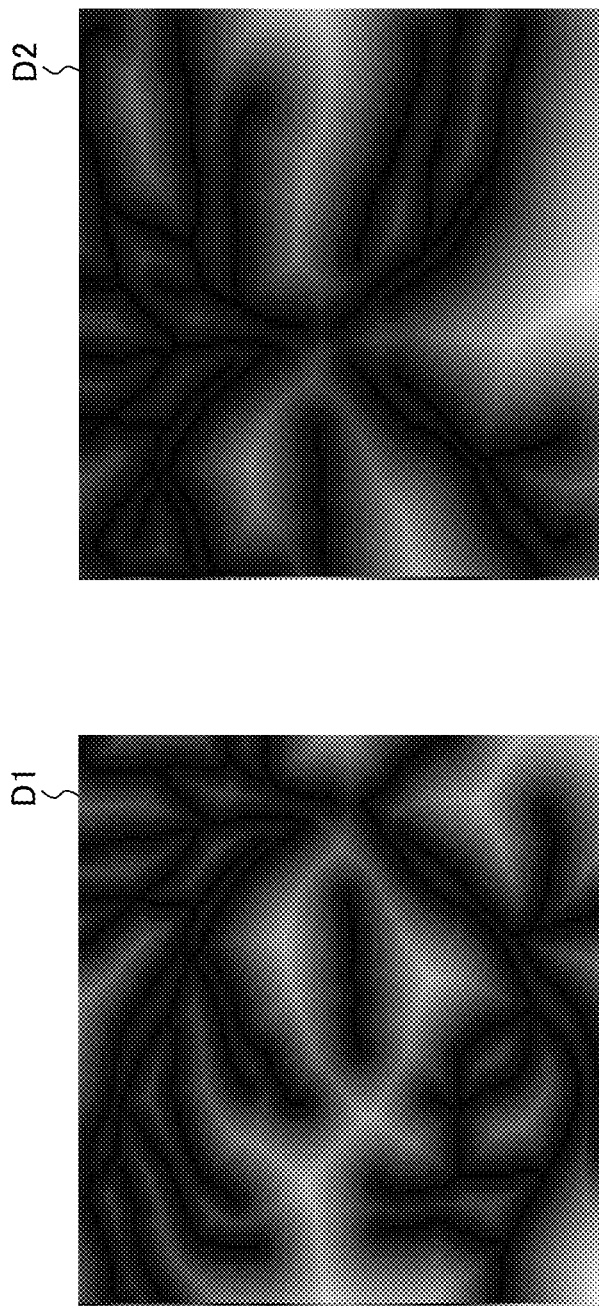

OPHTHALMOLOGICAL DEVICE, OPHTHALMOLOGICAL IMAGE PROCESSING METHOD, AND STORAGE MEDIUM

CROSS-REFERENCE TO RELATED APPLICATIONS

This application is a national stage (under 35 U.S.C. 371) of International Patent Application No. PCT/JP2018/019068, filed May 17, 2018 claiming priority to Japanese Patent Application No. 2017-120944, filed Jun. 21, 2017, both of which are herein incorporated by reference in their entirety.

FIELD

The present disclosure relates generally to an ophthalmological device, an ophthalmological image processing method and a storage medium.

BACKGROUND

Diagnostic imaging serves an important role in the field of ophthalmology. In recent years, utilization of optical coherence tomography (OCT) has advanced. OCT is being used not only for acquisition of B-scan images and three dimensional images of a subject's eye but also for acquisition of front images (en face images) such as C-scan images and shadowgrams. OCT is also utilized for acquisition of images in which a specific site of the subject's eye is emphasized, and for acquisition of functional information.

For example, B-scan images and front images in which eye fundus blood vessels such as retinal blood vessels and/or choroidal blood vessels are emphasized may be constructed based on time-series volume data acquired using OCT. Such images are referred to as blood vessel enhanced images, blood vessel emphasized images, or angiograms. This imaging technique (modality) is referred to as OCT angiography (OCTA). In addition, rendering techniques and graphical user interfaces (GUIs) for observing a desired slice of the subject's eye have been proposed.
PATENT DOCUMENT 1: Japanese Unexamined Patent Application Publication No. 2016-198447
NON-PATENT DOCUMENT 1: Daniel M. Schwarz et al., "Phase-Variance Optical Coherence Tomography: A Technique for Noninvasive Angiography", Ophthalmology Vol. 121, Number 1, January 2014

Although blood vessels are distributed over a wide area of the eye fundus, conventional OCTA can perform imaging only for a relatively narrow area.

An object of the present disclosure is to construct an angiogram over a wide area of the eye fundus.

SUMMARY

The first aspect of embodiments is an ophthalmological device that includes a memory, a detecting processor, an identifying processor, a transforming processor, and a composing processor. The memory stores a plurality of angiograms acquired by applying optical coherence tomography to a fundus of a subject's eye. The detecting processor is configured to detect a feature point from each of the plurality of angiograms. The identifying processor is configured to identify a plurality of feature point groups from among a plurality of feature points detected from the plurality of angiograms by the detecting processor, each of the plurality of feature point groups corresponding to a same site of the fundus. The transforming processor is configured to transform at least part of the plurality of angiograms based on the plurality of feature point groups identified by the identifying processor. The composing processor is configured to compose two or more angiograms of the plurality of angiograms at least part of which has been transformed by the transforming processor, based on the plurality of feature point groups.

The second aspect of embodiments is the ophthalmological device of the first aspect, wherein the transforming processor transforms at least one of a first angiogram and a second angiogram of the plurality of angiograms that include feature points belonging to a predetermined number or more of common feature point groups, to perform position matching between a feature point included in the first angiogram and a feature point included in the second angiogram.

The third aspect of embodiments is the ophthalmological device of the second aspect, wherein in the event that both the first angiogram and the second angiogram include feature points belonging to eight or more common feature point groups, the transforming processor performs a homography transformation based on eight or more feature points included in the first angiogram and eight or more feature points included in the second angiogram.

The fourth aspect of embodiments is the ophthalmological device of the second aspect, wherein in the event that both the first angiogram and the second angiogram include only feature points belonging to seven or less common feature point groups, the transforming processor performs a coordinate transformation different from a homography transformation based on seven or less feature points included in the first angiogram and seven or less feature points included in the second angiogram.

The fifth aspect of embodiments is the ophthalmological device of the fourth aspect, wherein in the event that both the first angiogram and the second angiogram include feature points belonging to six or more common feature point groups, the transforming processor performs an affine transformation based on six or more feature points included in the first angiogram and six or more feature points included in the second angiogram, or performs a Helmert transformation based on four or more feature points included in the first angiogram and four or more feature points included in the second angiogram.

The sixth aspect of embodiments is the ophthalmological device of the fourth aspect, wherein in the event that both the first angiogram and the second angiogram include feature points belonging to four or more common feature point groups, the transforming processor performs a Helmert transformation based on four or more feature points included in the first angiogram and four or more feature points included in the second angiogram.

The seventh aspect of embodiments is the ophthalmological device of any one of the second to sixth aspects, wherein the transforming processor performs a transformation of the second angiogram on the basis of the first angiogram at least once and a transformation of the first angiogram on the basis of the second angiogram at least once.

The eighth aspect of embodiments is the ophthalmological device of any one of the first to seventh aspects, wherein the composing processor composes the two or more angiograms by projecting the two or more angiograms onto a predetermined cylindrical surface.

The ninth aspect of embodiments is the ophthalmological device of any one of the first to seventh aspects, wherein the composing processor composes the two or more angiograms by projecting the two or more angiograms onto a predetermined spherical surface.

The tenth aspect of embodiments is the ophthalmological device of any one of the first to ninth aspects that further includes an edge detecting processor, and a distance image constructing processor. The edge detecting processor is configured to construct a plurality of edge images by applying an edge detection to each of the plurality of angiograms, in the event that a process performed by any of the detecting processor, the identifying processor, the transforming processor, and the composing processor has failed. The distance image constructing processor is configured to construct a plurality of distance images by applying a Hausdorff transformation to the plurality of edge images. The composing processor is configured to compose the two or more angiograms of the plurality of angiograms by applying registration to the plurality of distance images.

The eleventh aspect of embodiments is the ophthalmological device of any one of the first to tenth aspects, wherein the memory stores relative position information that represents a relative position between the plurality of angiograms. In addition, at least one of the detecting processor, the identifying processor, the transforming processor, and the composing processor performs a process based on the relative position information.

The twelfth aspect of embodiments is the ophthalmological device of any one of the first to eleventh aspects that further includes a data set acquisition device, and an image constructing processor. The data set acquisition device is configured to acquire a three dimensional data set by applying optical coherence tomography to the fundus. Further, the image constructing processor is configured to construct an angiogram based on the three dimensional data set acquired by the data set acquisition device. In addition, the memory stores the angiogram constructed by the image constructing processor.

The thirteenth aspect of embodiments is a method of processing an ophthalmological image includes the following steps: a step of storing a plurality of angiograms acquired by applying optical coherence tomography to a fundus of a subject's eye; a step of detecting a feature point from each of the plurality of angiograms; a step of identifying a plurality of feature point groups from among a plurality of feature points detected from the plurality of angiograms, each of the plurality of feature point groups corresponding to a same site of the fundus; a step of transforming at least part of the plurality of angiograms based on the plurality of feature point groups identified; and a step of composing two or more angiograms of the plurality of angiograms at least part of which has been transformed, based on the plurality of feature point groups.

To the method of processing an ophthalmological image of the thirteenth aspect, a method (step) implementable by the ophthalmological device of any one of the second to twelfth aspects may be added.

The fourteenth aspect of embodiments is a program configured to cause a computer to perform the method of processing an ophthalmological image of the thirteenth aspect. To the program of the fourteenth aspect, a program configured to cause the computer to perform a method implementable by the ophthalmological device of any one of the second to twelfth aspects may be added.

The fifteenth aspect of embodiments is a computer-readable storage medium storing the program of the fourteenth aspect. The computer-readable storage medium may further store a program configured to cause the computer to perform a method implementable by the ophthalmological device of any one of the second to twelfth aspects.

Any one or more of the matters described in the aspects described later can be added to any of the first to fifteenth aspects.

According to some aspects, an angiogram over a wide area of the eye fundus may be constructed.

BRIEF DESCRIPTION OF THE DRAWINGS

FIG. 7B is a schematic diagram for describing an example of the operation of the ophthalmological device according to the exemplary embodiment.

DETAILED DESCRIPTION OF THE EMBODIMENTS

Figure 1:
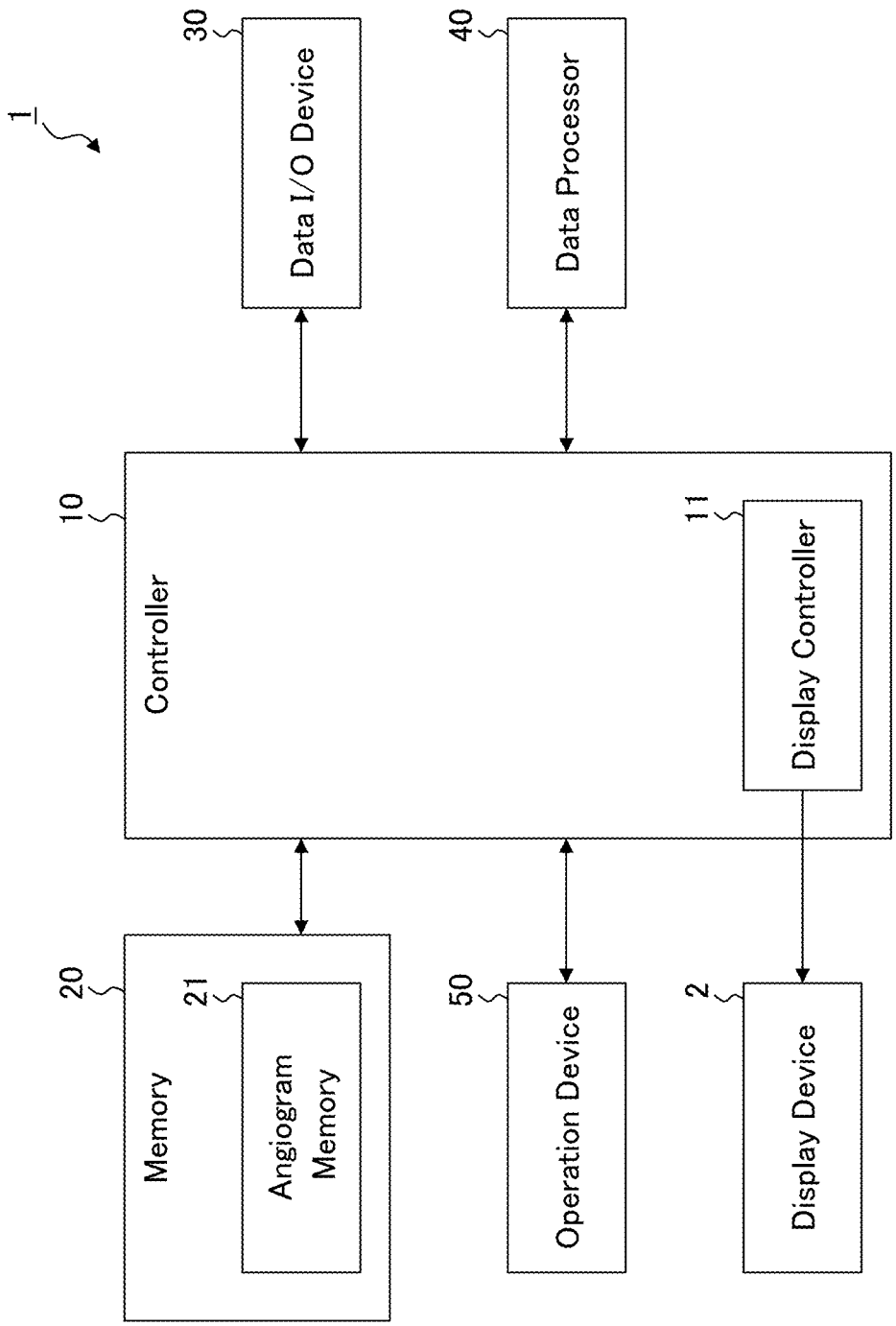
FIG. 1 is a schematic diagram illustrating an example of the configuration of the ophthalmological device according to the exemplary embodiment.

Some exemplary embodiments of the present invention will be described with referring to the drawings. It should be noted that any contents, matters or items described in the documents cited herein and any existing techniques or technologies may be incorporated in some exemplary embodiments.

Hereinafter, ophthalmological devices, ophthalmological image processing methods, programs, and storage media according to some exemplary embodiments will be described. Some exemplary ophthalmological image processing methods may be realized by some exemplary ophthalmological devices. An exemplary ophthalmological device may be a single apparatus (e.g., a computer including a storage device) or may include two or more apparatuses (e.g., one or more computers, one or more storage devices, and the like) that can communicate with each other.

Hardware and software for implementing an exemplary ophthalmological image processing method are not limited to the ophthalmological devices exemplified below, and may include a combination of arbitrary hardware and arbitrary software that contributes to the implementation.

An exemplary program causes a computer included in an exemplary ophthalmological device or the like to execute an exemplary ophthalmological image processing method. An exemplary storage medium is a computer-readable storage medium and records an exemplary program. An exemplary storage medium is a non-transitory storage medium. An exemplary storage medium may be an electronic medium using magnetism, light, photomagnetism, semiconductor, or the like. Typically, an exemplary storage medium includes a magnetic tape, a magnetic disk, an optical disk, a magneto-optical disk, a flash memory, a solid state drive, or the like.

<First Embodiment>

The ophthalmological device according to the first embodiment will be described. The ophthalmological device 1 illustrated in FIG. 1 may display various kinds of information such as images of the fundus of the subject's eye on the display device 2. The display device 2 may be a part of the ophthalmological device 1 or may be an external device connected to the ophthalmological device 1.

The ophthalmological device 1 includes the controller 10, the memory 20, the data input and output (I/O) device 30, the data processor 40, and the operation device 50. An ophthalmological devices in some other exemplary embodiments may not include the operation device 50.

(Controller 10)

The controller 10 is configured to control each part of the ophthalmological device 1. The controller 10 includes one or more processors. In the present specification, the term "processor" is used to mean, for example, a circuit such as a central processing unit (CPU), a graphics processing unit (GPU), an application specific integrated circuit (ASIC), a programmable logic device (e.g., a simple programmable logic device (SPLD), a complex programmable logic device (CPLD), a field programmable gate array (FPGA)), or the like. The controller 10 realizes some functions according to the present embodiment, for example, by reading out and executing one or more programs stored in one or more storage circuits and/or one or more storage devices (e.g., the memory 20).

The controller 10 includes the display controller 11. The display controller 11 is configured to execute control for displaying information on the display device 2. In some other exemplary embodiments, an ophthalmological device may not include the display controller 11.

(Memory 20)

The memory 20 stores various kinds of information. In the present example, the angiogram memory 21 is provided in the memory 20, and the angiogram memory 21 stores a plurality of angiograms obtained by applying OCT angiography to the fundus of the subject's eye. The memory 20 includes one or more storage devices such as a hard disk drive.

Although not shown in the drawings, in some exemplary embodiments, the memory 20 stores templates of screens, dialogs, icons, and other types of objects, which are displayed and used as GUIs on the display device 2. In addition, the memory 20 stores one or more programs executed for image data processing and one or more programs executed for controlling the GUIs. The processes according to the present embodiment are implemented by a cooperation of software including such programs and hardware including one or more processors.

(Data Input and Output Device 30)

The data input and output device 30 is configured to perform input of data into the ophthalmological device 1 and output of data from the ophthalmological device 1. The data input and output device 30 of some examples may include a communication device for performing data transmission and data reception via a communication line such as a local area network (LAN), the Internet, a dedicated line, etc. The data input and output device 30 of some examples may include a reader writer device for reading data from a storage medium and writing data into a storage medium. Further, the data input and output device 30 of some examples may include an image scanner that scans information recorded on a print medium or the like, a printer that records information on a paper medium, or other types of devices.

(Data Processor 40)

The data processor 40 includes one or more processors and executes various kinds of data processing. For example, the data processor 40 is configured to apply image processing to ophthalmological image data. In some examples, the data processor 40 may perform rendering such as three dimensional computer graphics (3DCG).

For example, when a three dimensional data set (e.g., volume data, stack data) of the subject's eye has been input to the ophthalmological device 1, the data processor 40 may apply various kinds of rendering to the three dimensional data set to generate a B-scan image (also referred to as a longitudinal cross sectional image or an axial cross sectional image), a C-scan image (also referred to as a transverse cross sectional image or a horizontal cross sectional image), a projection image, a shadowgram, or other types of images. An image of an arbitrarily-designated cross section such as a B-scan image or a C-scan image is constructed by, for example, selecting image elements (pixels, voxels) on the designated cross section from the three dimensional data set. In some other examples, an image of an arbitrarily-designed cross section may be constructed from an arbitrarily-set slice of the three dimensional data set. A projection image is constructed by projecting (integrating) the three dimensional data set in a predetermined direction. Here, the projection direction may be the Z direction (also referred to as the depth direction or the axial direction). A shadowgram is constructed by projecting (integrating) a part of the three dimensional data set in a predetermined direction. Here, the part projected is, for example, partial data of the three dimensional data set corresponding to a specific layer (slab). An image that is viewed from the front side of the subject's eye, such as a C-scan image, a projection image, or a shadowgram, is referred to as a front image (also referred to as an en face image).

The data processor 40 may be capable of executing various kinds of image processing in addition to rendering. For example, although details will be described later, the data processor 40 may be configured to construct a so-called panoramic image by composing a plurality of angiograms stored in the angiogram memory 21. In addition, the data processor 40 may be configured to perform segmentation and/or size analysis. The segmentation is image processing for identifying a specific tissue or a specific tissue boundary. The size analysis is image processing for determining (calculating) the size of a specific tissue. The size of a tissue is, for example, layer thickness or volume. In the event that a specific layer (or a specific layer boundary) is identified by segmentation, the data processor 40 may perform B-scan image reconstruction or front image reconstruction so that the specific layer identified becomes flat. Such an image is referred to as a flattened image.

Some detailed configurations of the data processor 40 will be described later.

(Operation Device 50)

The operation device 50 is used by the user to input instructions and information into the ophthalmological device 1. The operation device 50 may include any kinds of existing operation devices usable together with a computer. For example, the operation device 50 may include a pointing device such as a mouse, a touch pad, or a track ball. The operation device 50 may include a keyboard, a pen tablet, a dedicated operation panel, or other devices.

(On Angiograms)

As described above, the ophthalmological device 1 is configured to process angiograms. An angiogram is an image of the eye fundus constructed by: analyzing images acquired through OCT scans to identify image regions corresponding to blood vessels (referred to as blood vessel regions); and changing the representation aspects of the identified blood vessel regions to emphasize (enhance, highlight) the blood vessel regions. The identification of the blood vessel regions is performed using a plurality of images acquired by repeatedly applying OCT scanning to substantially the same area of the subject's eye. In the present embodiment, for example, an angiogram is stored in the angiogram memory 21 as a front image. Such a front image is referred to as a blood vessel emphasized front image herein. In some other examples, one or more three dimensional data sets usable for angiogram construction may be stored in the angiogram memory 21. In such a case, the ophthalmological device 1 (e.g., the data processor 40) includes known hardware and software for constructing an angiogram from a three dimensional data set.

There are several types of methods for angiogram construction. Some examples thereof are described herein. Note that one or more parts or all of the plurality of steps included in the method described below may be performed by the data processor 40. In addition or instead, one or more parts or all of the plurality of steps included in the method described below may be performed by one or more devices other than the ophthalmological device 1 (e.g., a computer, other ophthalmological device).

To begin with, repetitive scanning (iterative scanning) is applied to each of a plurality of B-scan cross sections of the fundus of the subject's eye, to create a three dimensional data set that includes a plurality of B-scan images arranged in time series (along the time axis) for each of the B-scan cross sections. Fixation and tracking are known as methods for realizing the repetitive scanning of substantially the same B-scan cross section. The three dimensional data set at this stage may be stored in the angiogram memory 21.

Next, position matching (registration) of the B-scan images is performed for each B-scan cross section. The position matching is performed, for example, by using any known image matching technique. An example of the position matching includes extraction of a feature region from each of the B-scan images for a B-scan cross section, and position matching of the B-scan images via position matching of the feature regions respectively extracted from the B-scan images. The three dimensional data set at this stage may be stored in the angiogram memory 21.

Subsequently, a process of identifying image regions that change between the B-scan images having registered. This identification includes, for example, a process of determining the differences between different B-scan images. Each B-scan image is brightness image data representing the morphology (structure) of the subject's eye, and it can be considered that an image region therein corresponding to a non-blood-vessel site is substantially invariant. On the other hand, considering a phenomenon that the backscattering contributing to interference signals randomly varies under the influence of blood flow, an image region in which a change has occurred between the registered B-scan images may be regarded as a blood vessel region. Here, the image region with the change includes, for example, pixels with non-zero difference or pixels with difference equal to or larger than a predetermined threshold. The three dimensional data set at this stage may be stored in the angiogram memory 21.

To the image regions identified in this way, information indicating that the image regions are blood vessel regions may be assigned. In other words, the pixel values of the identified image regions may be changed. Thereby, an angiogram is obtained. The angiogram thus constructed may be stored in the angiogram memory 21.

(Configuration Examples of Data Processor 40)

Figure 2:
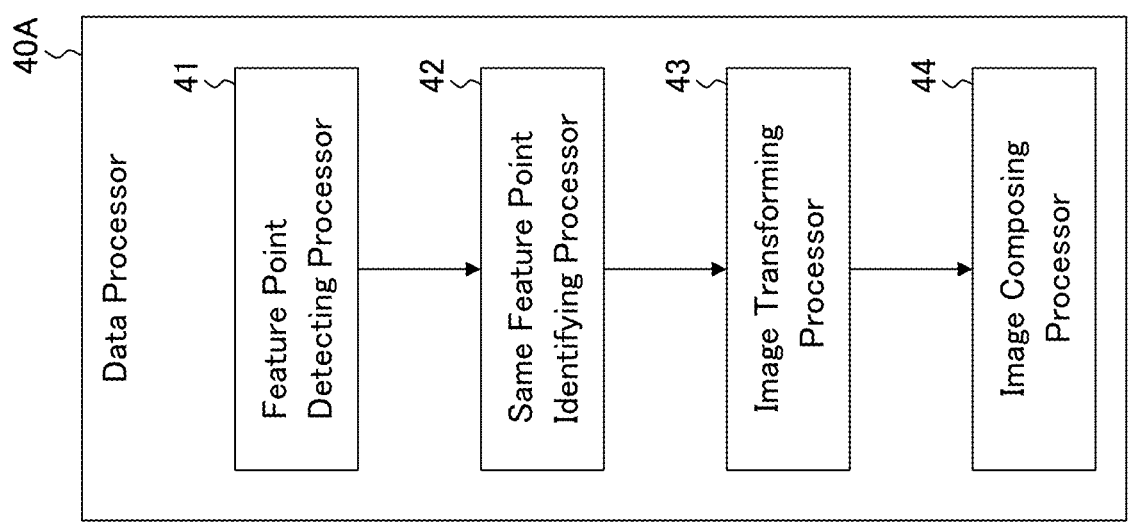
FIG. 2 is a schematic diagram illustrating an example of the configuration of the ophthalmological device according to the exemplary embodiment.

The data processor 40A shown in FIG. 2 is an example of the data processor 40. The data processor 40A of the present example includes the feature point detecting processor 41, the same feature point identifying processor 42, the image transforming processor 43, and the image composing processor 44.

(Feature Point Detecting Processor 41)

The feature point detecting processor 41 is configured to detect a feature point from each of the angiograms stored in the memory 20. In other words, the feature point detecting processor 41 is configured to analyze an angiogram to identify a feature site depicted in the angiogram.

The feature point detection may be executed using a known method, for example. Examples of known feature point detection methods include the followings: Features from Accelerated Segment TEST (FAST); Oriented FAST Rotated Brief (ORB); Binary Robust Invariant Scalable Keypoints (BRISK); Maximally Stable Extremal Regions (MSER); Good Features to Track (GFTT); HARRIS; SimpleBlob; KAZE; and Accelerated KAZE.

The feature point detecting processor 41 thus configured may detect an edge of a tissue depicted in an angiogram, and in particular, a branch point or the like of a blood vessel. To each feature point detected, a feature amount obtained by the applied method is assigned.

(Same Feature Point Identifying Processor 42)

The same feature point identifying processor 42 is configured to identify a plurality of feature point groups from among the feature points detected from the angiograms by the feature point detecting processor 41. Here, each of the feature point groups corresponds to the same site of the eye fundus. Hereinafter, this process will be described in a more specific manner.

As described above, the plurality of angiograms are stored in the angiogram memory 21. The M number of angiograms stored in the angiogram memory 21 are represented by the symbols $G_1, G_2, \ldots, G_M$. Here, M is an integer equal to or greater than 2.

The feature point detecting processor 41 is configured to detect feature points from the angiogram $G_m$ (m=1, 2, ..., M). In the present example, the N (m) number of feature points $P_{m1}, P_{m2}, \ldots, P_{mN(m)}$ are detected from the angiogram $G_m$. In general, the numbers of detected feature points N(1), N(2), ..., N(M) respectively for the angiograms $G_1$, $G_2, \ldots, G_M$ are different. Note that some examples may be configured to detect a predetermined number of feature points from each angiogram Gm.

The same feature point identifying processor 42 may be configured to identify a plurality of feature point groups $Q_1$, $Q_2, \ldots, Q_K$ corresponding to different sites of the eye fundus $A_1, A_2, \ldots, A_K$, from among the feature points $\{P_{11}, P_{12}, \ldots, P_{1N(1)}\}, \{P_{21}, P_{22}, \ldots, P_{2N(2)}\}, \ldots, \{P_{M1}, P_{M2}, \ldots, P_{MN(M)}\}$ detected from the angiograms $G_1$, $G_2, \ldots, G_M$ by the feature point detecting processor 41. The site $A_k$ is, for example, a branch point of a blood vessel.

The feature point group $Q_k$ (k=1, 2, ..., K) includes one or more feature points corresponding to the site $A_k$, among the feature points $P_{11}, \ldots, P_{MN(M)}$. Further, in the case where the feature point group $Q_k$ includes a plurality of feature points, the feature points are originated from different angiograms.

The same feature point identifying processor 42 may be configured to perform the above feature point classification, for example, based on the feature amounts assigned to the feature points $P_{11}, \ldots, P_{MN(M)}$. In some examples, the same feature point identifying processor 42 is configured to search for a group of feature points having the same feature amount value, from among the feature points $P_{11}, \ldots, P_{MN(M)}$. The feature point group search is performed by a brute-force method, for example. More specifically, the feature point group search may be realized by performing comparisons of feature amount values for all the pairs out of the feature points $P_{11}, \ldots, P_{MN(M)}$.

The feature point classification applicable to some aspects is not limited to the process of searching for a group of feature points having the same feature amount value. For example, the feature point classification may be performed by searching for a group of feature points such that a difference in the feature amount values is included in a predetermined range.

As yet another example, the feature point classification may be performed based on information about the vicinities of feature points, instead of or in addition to considering their feature amount values. Here, the information about the vicinities of feature points may include pixel values, shapes, patterns, or the like. In general, the same feature point identifying processor 42 may use any technique for determining the similarities and/or differences between feature points.

(Image Transforming Processor 43)

The image transforming processor 43 is configured to transform (deform) at least part of the angiograms ($G_1$, $G_2, \ldots, G_M$) based on the feature point groups ($Q_1$, $Q_2, \ldots, Q_K$) identified by the same feature point identifying processor 42. Here, "at least part of the angiograms" may include any one or more of the angiograms, and/or one or more partial images of any one or more of the angiograms.

In the present embodiment, for example, the image transforming processor 43 may be configured to transform at least one of a pair of angiograms (referred to as the first angiogram and the second angiogram) of the angiograms ($G_1, G_2, \ldots, G_M$) that include feature points belonging to a predetermined number or more of common feature point groups (i.e., a predetermined number or more of feature point groups out of the feature point groups $Q_1, Q_2, \ldots, Q_K$), to perform position matching between the feature points in the first angiogram and the feature points in the second angiogram.

Here, the predetermined number described above may be set in an arbitrary manner. In addition, the first angiogram and the second angiogram having feature points belonging to a common feature point group, include common regions. The common regions correspond to the same area of the eye fundus. That is, part of the first angiogram and part of the second angiogram represent the same area of the eye fundus. Such image transformation is image processing of relatively transforming the first angiogram and the second angiogram to match the morphology (e.g., size, orientation, shape, etc.) of the site depicted in the common regions.

The predetermined number described above (i.e., the number of common feature point groups) corresponds to the number of the unknowns of an equation for determining a coordinate transformation for angiogram transformation. For example, in the event that the number of common feature point groups between the first angiogram and the second angiogram is eight or more, a homography transformation may be applied as the coordinate transformation. In the event that the number is six or more, an affine transformation may be applied. In the event that the number is four or more, a Helmert transformation may be applied. Note that coordinate transformations applicable to embodiments are not limited to the above specific examples, and any known coordinate transformation may be applied.

The affine transformation is defined by an affine mapping for performing rotation, translation, and scaling of an image. The affine transformation is defined by the equation (1) shown below, and its transformation matrix includes six unknowns. It should be noted that the Helmert transformation is the coordinate transformation of four unknowns obtained by setting "d=a" and "c=−b" in the following affine equation (1).

$$\begin{pmatrix} x_2 \\ y_2 \\ 1 \end{pmatrix} = \begin{pmatrix} a & b & t_x \\ c & d & t_y \\ 0 & 0 & 1 \end{pmatrix} \begin{pmatrix} x_1 \\ y_1 \\ 1 \end{pmatrix} \quad (1)$$

The Homography transformation (plane projection transformation) is a coordinate transformation capable of setting a scaling ratio (enlargement ratio, reduction ratio) for each coordinate position in addition to the affine transformation. The homography transformation is defined by the following equation (2), and its transformation matrix includes eight unknowns.

$$\begin{pmatrix} sx_2 \\ sy_2 \\ s \end{pmatrix} = \begin{pmatrix} h_{11} & h_{12} & h_{13} \\ h_{21} & h_{22} & h_{23} \\ h_{31} & h_{32} & 1 \end{pmatrix} \begin{pmatrix} x_1 \\ y_1 \\ 1 \end{pmatrix} \quad (2)$$

In the event that the number of common feature point groups between the first and second angiograms is eight or more, that is, the number of feature points corresponding to the same site of the eye fundus (i.e., the number of same feature points) is eight or more, the image transforming processor 43 may apply the homography transformation to relatively transform the first angiogram and the second angiogram. In this process, for example, for each of the same feature point, the coordinate value in the first angiogram is substituted into ($x_1$, $y_1$) of the equation (2), and the coordinate value in the second angiogram is substituted into ($x_2$, $y_2$) of the equation (2). Thereby, eight (or more) equations having unknowns $h_{11}$ to $h_{32}$ is created. Solving the simultaneous equations gives the eight unknowns $h_{11}$ to $h_{32}$. The image transforming processor 43 may be configured to execute such computing operations.

Likewise, in the case where the affine transformation or the Helmert transformation is employed, the image transforming processor 43 may obtain a transformation matrix by forming simultaneous equations and solving the simultaneous equations.

The image transforming processor 43 may apply the above processing for each pair of angiograms having the same feature point. The same coordinate transformation may be applied to all pairs of angiograms, or coordinate transformations may be selected according to the numbers of the same feature points. Further, a coordinate transformation may be applied only to pairs having a predetermined number or more of the same feature points.

In some exemplary embodiments, the image transforming processor 43 may be configured to operate in the following way. First, in the event that both the first angiogram and the second angiogram include feature points belonging to eight or more common feature point groups, the image transforming processor 43 performs the homography transformation based on eight or more feature points included in the first angiogram and eight or more feature points included in the second angiogram.

On the other hand, in the event that both the first angiogram and the second angiogram include only feature points belonging to common feature point groups of seven or less, the image transforming processor 43 performs a coordinate transformation different from the homography transformation, based on seven or less feature points included in the first angiogram and seven or less feature points included in the second angiogram. If this is the case and also in the event that both the first angiogram and the second angiogram include feature points belonging to six or seven common feature point groups, the image transforming processor 43 performs the affine transformation based on six or seven feature points included in the first angiogram and six or seven feature points included in the second angiogram. On the other hand, in the event that both the first angiogram and the second angiogram include feature points belonging to four or five common feature point groups, the image transforming processor 43 performs the Helmert transformation based on four or five common feature points included in the first angiogram and four or five feature points included in the second angiogram.

As described above, the image transforming processor 43 is configured to transform any one or both of the first angiogram and the second angiogram. In the present embodiment, the image transforming processor 43 may be configured to perform a transformation of the second angiogram on the basis of the first angiogram (referred to as the first image transformation) at least once, and a transformation of the first angiogram on the basis of the second angiogram (referred to as the second image transformation) at least once. Such image transformation processing can improve the accuracy and precision of image matching between the first angiogram and the second angiogram.

The number of times of execution of the first image transformation and that of the second image transformation may be arbitrary. The number of times of execution of the first image transformation and that of the second image transformation may be the same or different. The number of times of execution of image transformation may be set in advance. Alternatively, the first image transformation and the second image transformation may be performed alternately and repeatedly until the image matching between the first angiogram and the second angiogram converges (within a predetermined range).

(Image Composing Processor 44)

The image composing processor 44 composes (merges) two or more angiograms of the angiograms ($G_1, G_2, \ldots, G_M$) at least part of which has been transformed by the image transforming processor 43, based on the feature point groups ($Q_1, Q_2, \ldots, Q_K$) identified by the same feature point identifying processor 42.

In the present embodiment, when composing the first angiogram and the second angiogram, the image composing processor 44 may determine the positions of the first angiogram and the second angiogram so as to match part or all of the same feature points included in the first and second angiograms, and then compose the first angiogram and the second angiogram. In other words, the image composing processor 44 may paste the first angiogram and the second angiogram together using the same feature points as positioning references and also using their common regions as "pasting margins".

In some other examples, the image composing processor 44 may be configured to perform the positioning (registration) between the first angiogram and the second angiogram so that the sum of errors in the same feature points becomes minimum. Here, the sum is, for example, the simple sum, the sum of squares, the square root of sum of squares, or other kinds of sum. Alternatively, the image composing processor 44 may be configured to perform the positioning (registration) between the first angiogram and the second angiogram so that the sum of errors in the same feature points becomes equal to or less than a predetermined threshold. It should be noted that image positioning methods (applicable image registration methods) applicable to embodiments are not limited to the above examples, and any known methods may be applied.

The image composing processor 44 may be configured to transform a composite image (panoramic image) of two or more angiograms, for example, according to the shape of the eye fundus (the surface thereof). For example, the image composing processor 44 may be configured to project two or more angiograms onto a predetermined cylindrical surface to compose the angiograms. Alternatively, the image composing processor 44 may be configured to project two or more angiograms onto a predetermined spherical surface to compose the angiograms. In addition, surfaces onto which two or more angiograms are projected are not limited to cylindrical surfaces or spherical surfaces, and a projection surface of an arbitrary shape may be employed. For example, in the event that the shape of the fundus (its surface) of the subject's eye has already been obtained using OCT or other techniques, the projection surface of the eye fundus shape may be employed.

[Operation]

Figure 3:
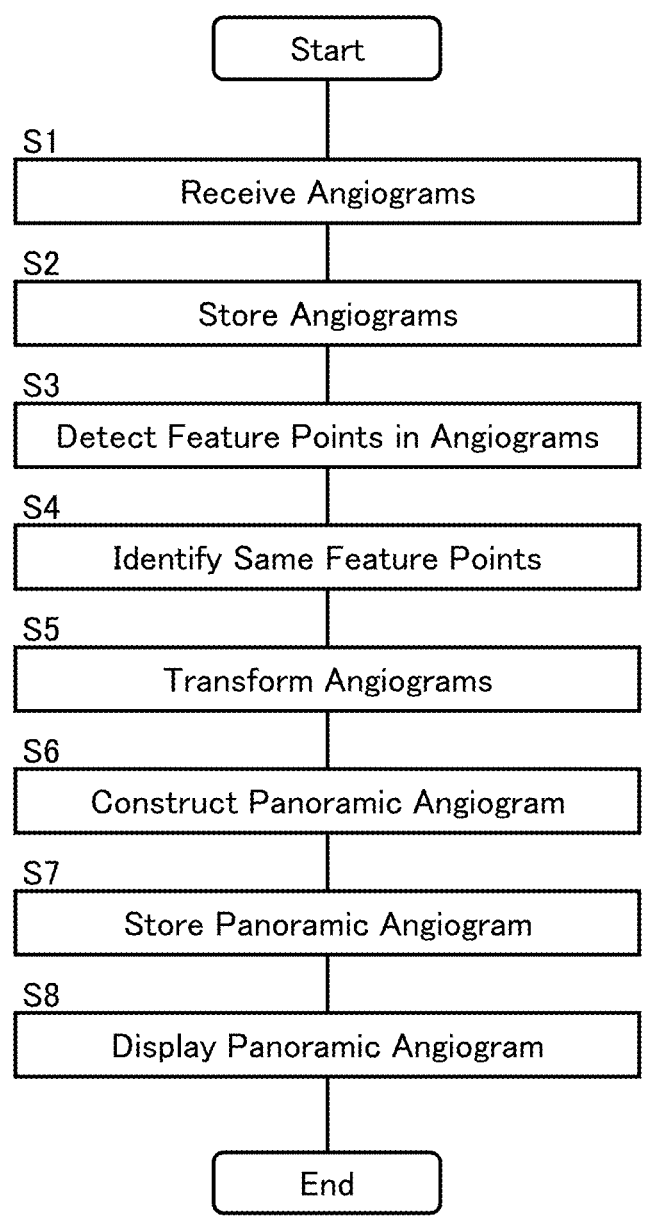
FIG. 3 is a flowchart illustrating an example of the operation of the ophthalmological device according to the exemplary embodiment.

Some examples of the operation of the ophthalmological device 1 according to the present embodiment will be described. FIG. 3 shows an example of the operation flow of the ophthalmological device 1.

(S1: Receive Angiograms)

First, OCT angiography is applied to the fundus of the subject's eye, and a plurality of angiograms are constructed. The angiograms are images depicting a plurality of different regions in the eye fundus. OCT scans of the eye fundus in the OCT angiography are performed using an ophthalmological imaging apparatus having an OCT function. The construction of the angiograms based on the data acquired by the OCT scans is performed by the ophthalmological imaging apparatus or other apparatus.

The constructed angiograms are, for example, sent directly or indirectly to the ophthalmological device 1 or stored in an image archiving apparatus. In the latter case, the angiograms are sent directly or indirectly from the image archiving apparatus to the ophthalmological device 1. The ophthalmological device 1 receives the angiograms transmitted from the ophthalmological imaging apparatus or from the image archiving apparatus, by the data input and output device 30.

(S2: Store Angiograms)

Figure 4A:
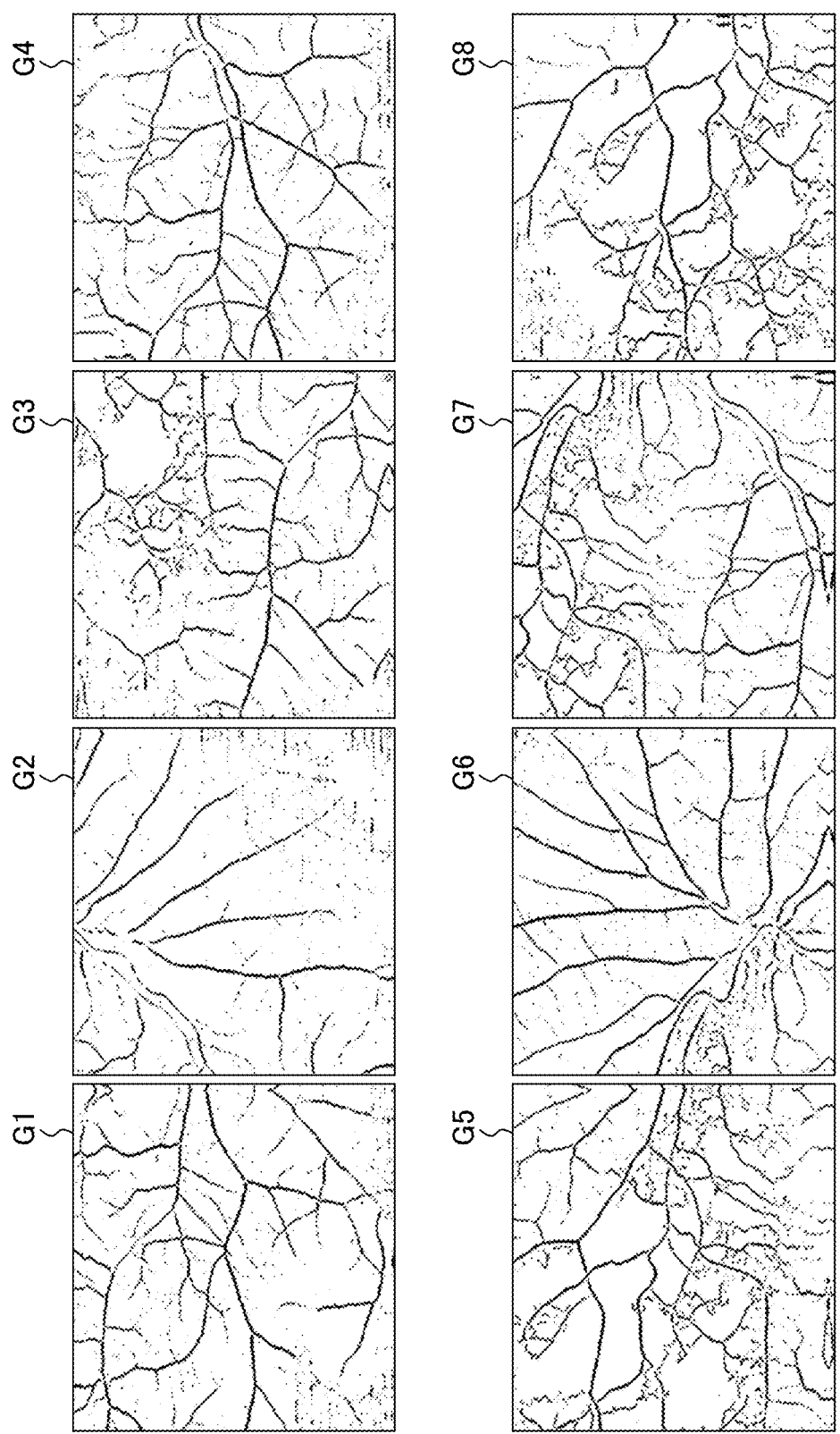
FIG. 4A is a schematic diagram for describing an example of the operation of the ophthalmological device according to the exemplary embodiment.

The controller 10 stores the angiograms received in the step S1 in the angiogram memory 21 provided in the memory 20. For example, the controller 10 reads out the angiograms in a predetermined order and sends the angiograms to the data processor 40 in the predetermined order. FIG. 4A shows the exemplary angiograms G1 to G8 to be processed by the ophthalmological device 1.

(S3: Detect Feature Points in Angiograms)

The feature point detecting processor 41 of the data processor 40 analyzes each of the angiograms stored in the angiogram memory 21 in the step S2, to detect feature points.

Figure 4B:
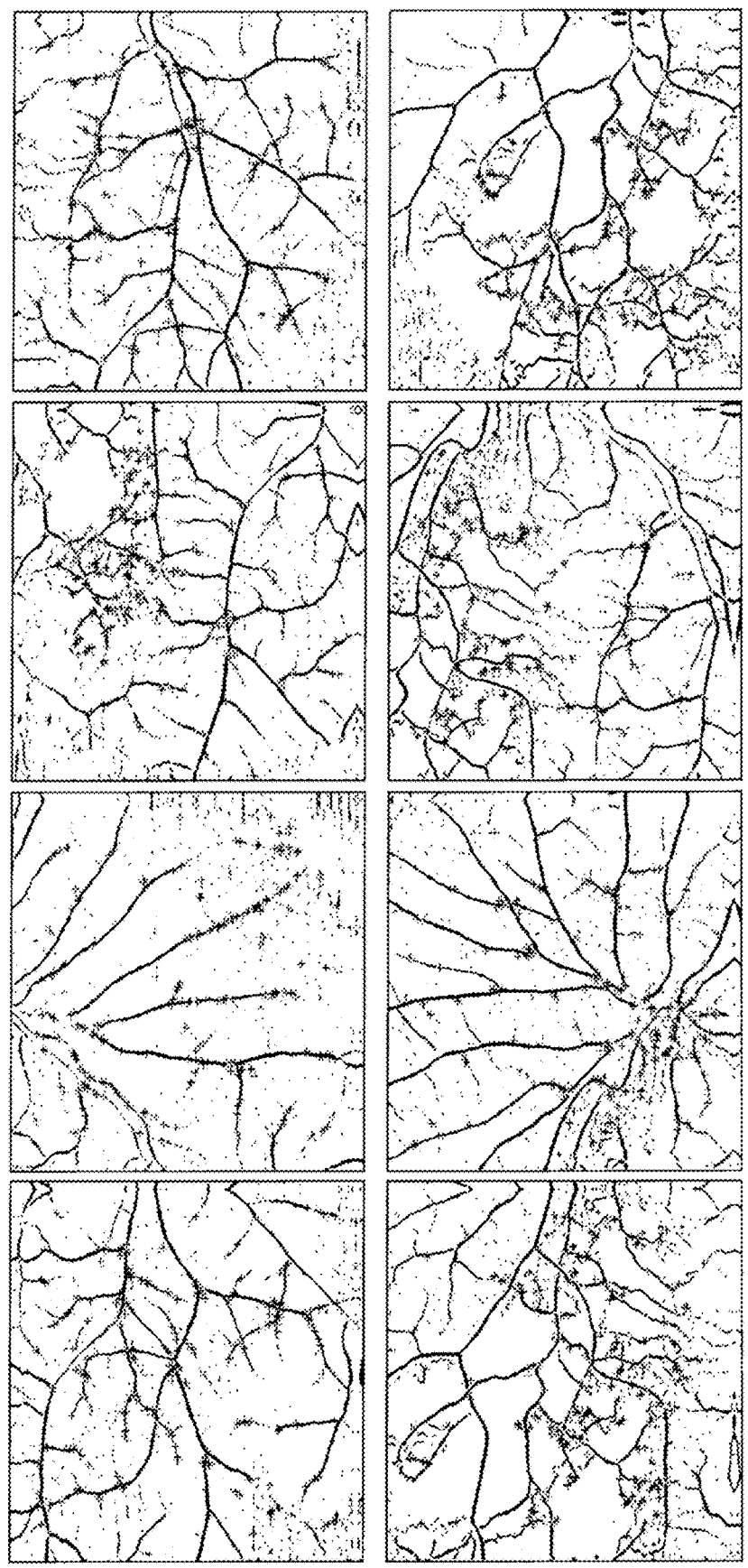
FIG. 4B is a schematic diagram for describing an example of the operation of the ophthalmological device according to the exemplary embodiment.

FIG. 4B shows the plurality of feature points detected from the angiograms G1 to G8 in the step S3. Here, each feature point is indicated by a cross mark. Although not shown in the drawings, a set of feature points detected from the angiogram Gm is represented by $\{P_{m1}, P_{m2}, \ldots, P_{mN(m)}\}$ (m=1, 2, . . . , 8).

(S4: Identify Same Feature Points)

The same feature point identifying processor 42 identifies a plurality of feature point groups from among the feature points detected from the angiograms in the step S3. Here, each of the feature point groups corresponds to the same site of the eye fundus. That is, the same feature point identifying processor 42 functions to identify the same feature points detected from different angiograms.

Figure 4C:
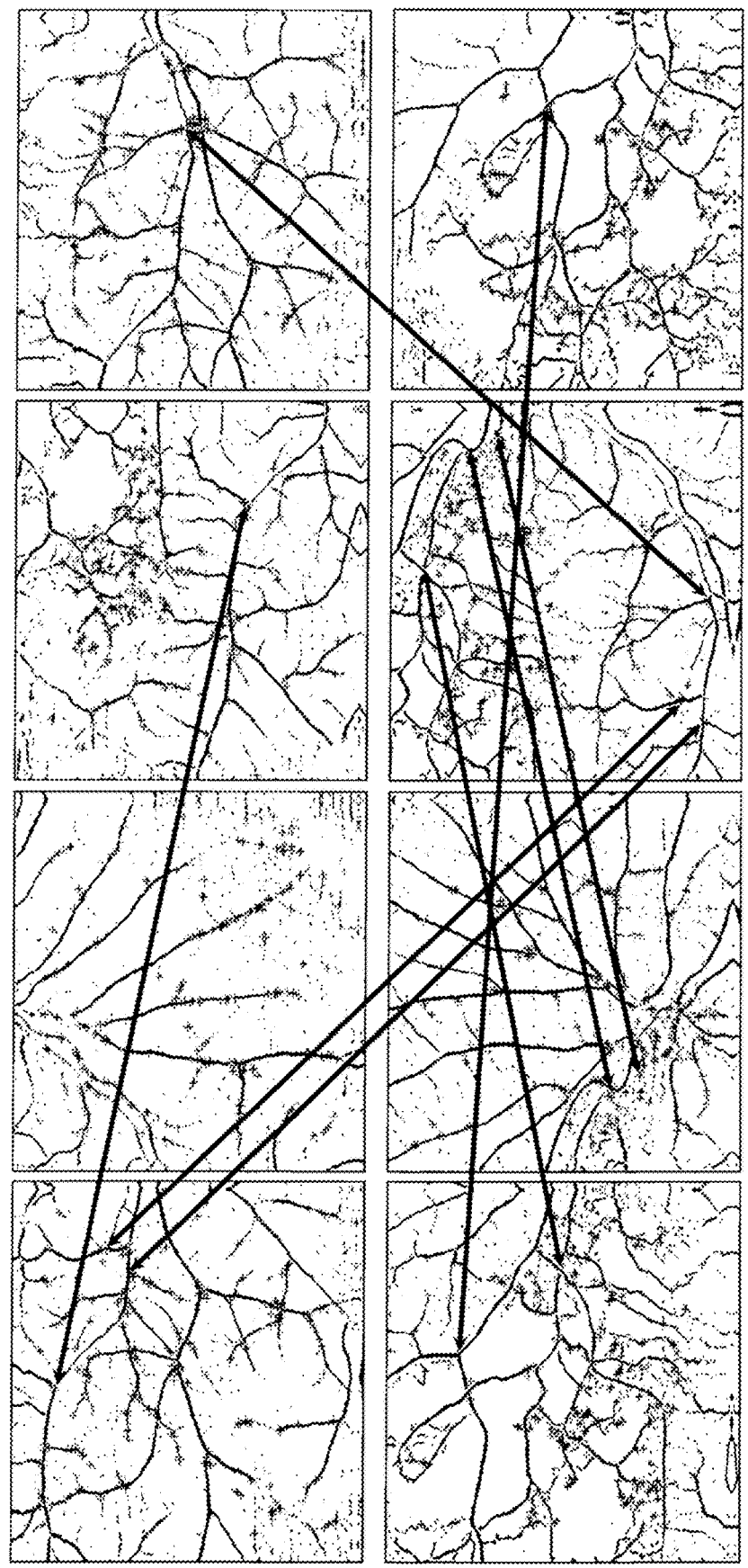
FIG. 4C is a schematic diagram for describing an example of the operation of the ophthalmological device according to the exemplary embodiment.

FIG. 4C shows the pairs of the same feature points identified in the step S4. Each pair of the corresponding same feature points is indicated by a two-way arrow (two direction arrow).

(S5: Transform Angiograms)

The image transforming processor 43 transforms at least part of the angiograms based on the feature point groups (i.e., the pairs of the same feature points) identified in the step S4.

(S6: Construct Panoramic Angiogram)

Based on the feature point groups (i.e., the pairs of the same feature points) identified in the step S4, the image composing processor 44 composes two or more angiograms of the angiograms at least part of which has been transformed in the step S5. Thereby, a panoramic angiogram is constructed.

In the present example, the image composing processor 44 composes two or more angiograms of the angiograms so as to place the same feature points in different angiograms paired in the step S4 at the same position in the resulting panoramic angiogram.

At this time, in the present example, an angiogram having no feature points paired with a feature point in another angiogram, is excluded from the image composition. That is, if every feature point detected from an angiogram is not included in the feature point groups identified in the step S5, the angiogram is excluded from the image composition. Accordingly, the panoramic angiogram obtained by the present example is constructed from angiograms each of which includes at least one feature point paired with a feature point in another angiogram.

Further, the image composing processor 44 may create a panoramic angiogram by projecting two or more angiograms onto a predetermined curved surface such as a cylindrical surface or a spherical surface.

(S7: Store Panoramic Angiogram)

The controller 10 stores the panoramic angiogram created in the step S6 in the memory 20.

(S8: Display Panoramic Angiogram)

Further, the display controller 11 displays the panoramic angiogram created in the step S6 on the display device 2.

Figure 4D:
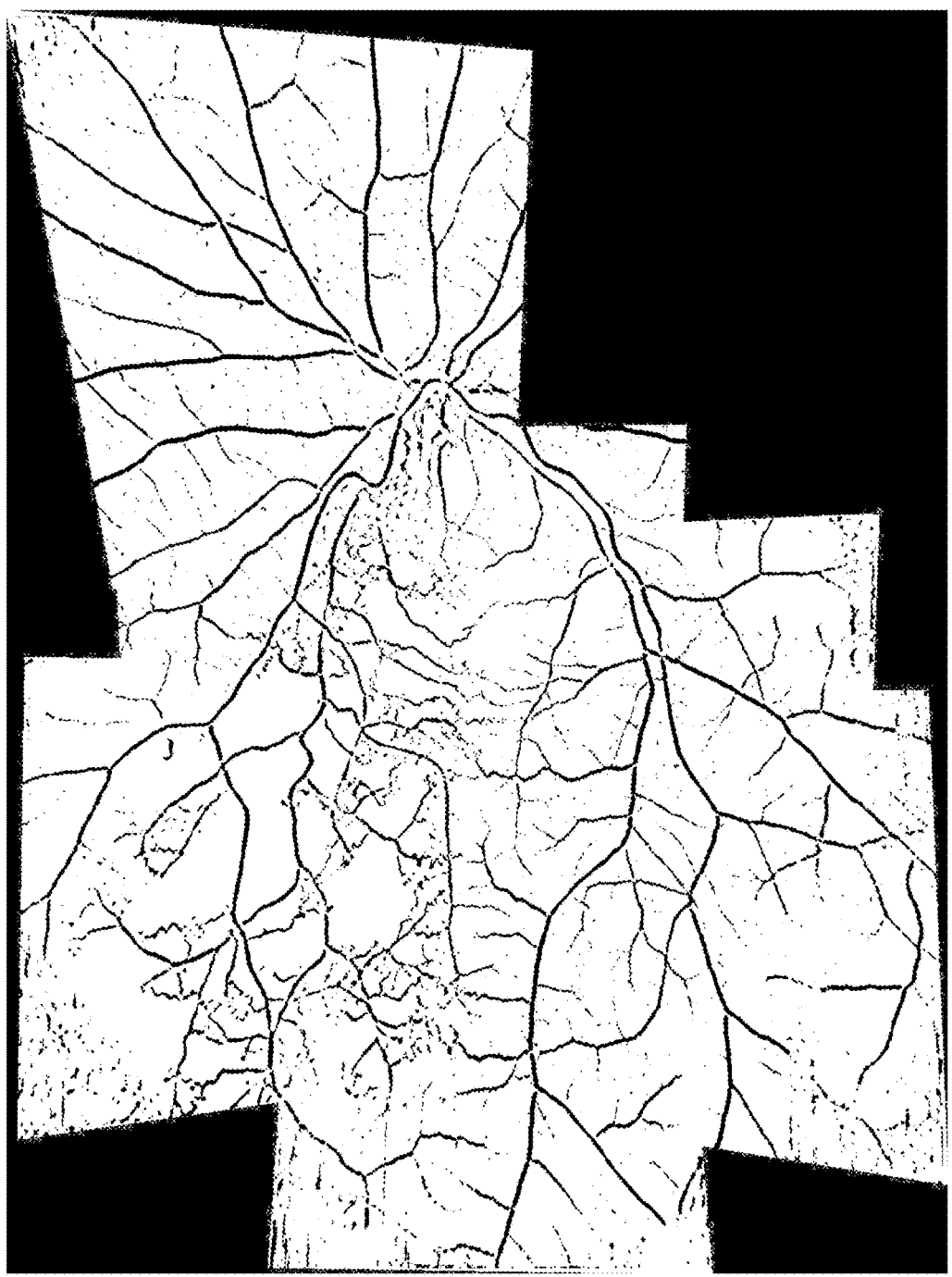
FIG. 4D is a schematic diagram for describing an example of the operation of the ophthalmological device according to the exemplary embodiment.

FIG. 4D shows an example of the panoramic angiogram displayed in the step S8. This panoramic angiogram is an image obtained by merging seven angiograms Gm (m=1, 3, . . . , 8) excluding the angiogram G2 of the eight angiograms G1 to G8 shown in FIG. 4A. Thus, the operation illustrated in FIG. 3 terminates (End).

Figure 5:
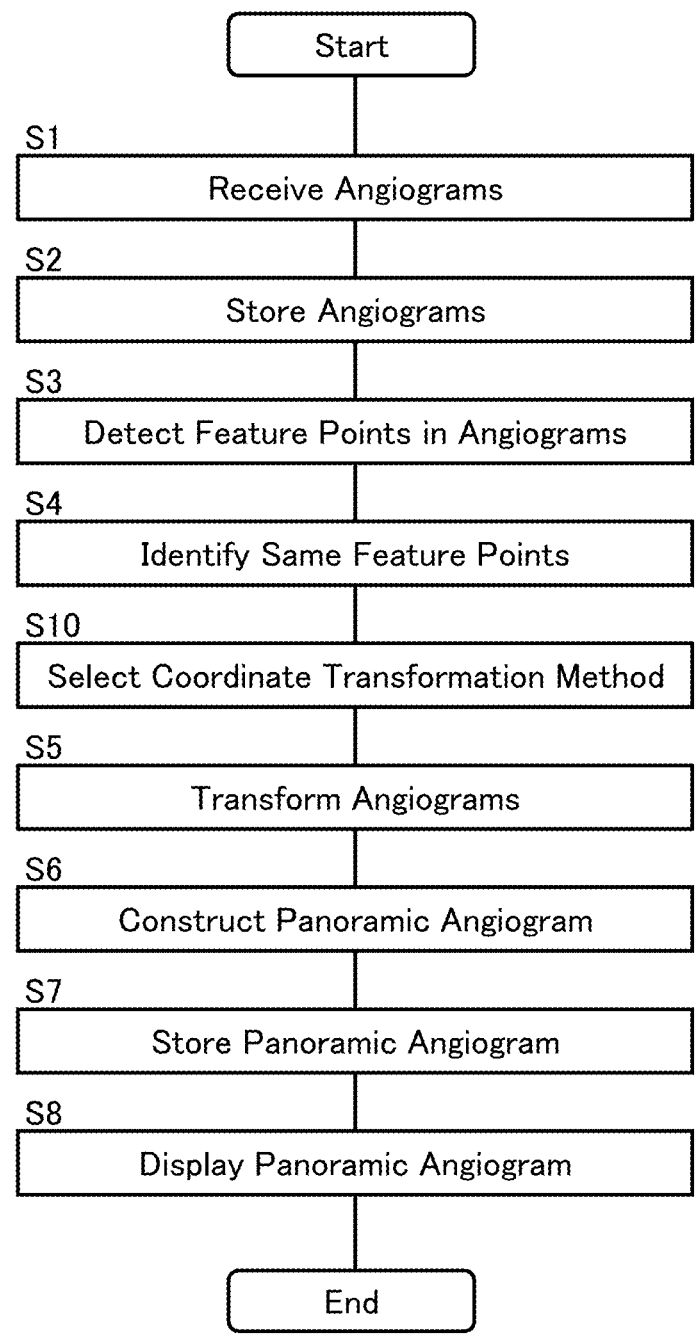
FIG. 5 is a flowchart illustrating an example of the operation of the ophthalmological device according to the exemplary embodiment.

FIG. 5 shows another example of the operation flow of the ophthalmological device 1. The operation flow shown in FIG. 5 is obtained by adding a new step S10 between the steps S4 and S5 of the operation flow shown in FIG. 3.

In the operation flow shown in FIG. 5, the steps S1 to S4 are carried out in the same manner as the steps S1 to S4 in FIG. 3. After the same feature points are identified in the step S4, the image transforming processor 43 selects a coordinate transformation method to be applied to the image transformation, based on the result of the step S4 (S10). For example, the image transforming processor 43 may select the homography transformation if the number of the common feature point groups between one pair of angiograms (the first angiogram and the second angiogram) is eight or more, select the affine transformation if the number is six or seven, or select the Helmert transformation if the number is four or five.

The image transforming processor 43 transforms at least part of the angiograms based on the feature point groups (i.e., the pairs of the same feature points) identified in the step S4 and based on the coordinate transformation method selected in the step S10 (S5). The steps S6 to S8 are executed in the same manner as the steps S6 to S8 in FIG. 3. Thus, the operation shown in FIG. 5 terminates (End).

[Actions and Effects]

Some actions and effects of the ophthalmological device 1 according to the present embodiment will be described.

The ophthalmological device 1 includes the memory (20), the detecting processor (the feature point detecting processor 41), the identifying processor (the same feature point identifying processor 42), the transforming processor (the image transforming processor 43), and the composing processor (the image composing processor 44).

The memory (20) is configured to store a plurality of angiograms ($G_1$ to $G_M$) acquired by applying optical coherence tomography to the fundus of the subject's eye.

The detecting processor (the feature point detecting processor 41) is configured to detect one or more feature points ($P_{mN(m)}$) from each of the plurality of angiograms ($G_m$).

The identifying processor (the same feature point identifying processor 42) is configured to identify a plurality of feature point groups ($Q_1$ to $Q_K$) from among the plurality of feature points ($P_{11}$ to $P_{MN(M)}$) detected from the plurality of angiograms ($G_1$ to $G_M$) by the detecting processor. Here, the plurality of feature point groups ($Q_1$ to $Q_K$) correspond to a plurality of sites ($A_1$ to $A_K$) of the eye fundus, respectively.

The transforming processor (the image transforming processor 43) is configured to transform at least part of the plurality of angiograms ($G_1$ to $G_M$) based on the plurality of feature point groups ($Q_1$ to $Q_K$) identified by the identifying processor.

The composing processor (the image composing processor 44) is configured to compose two or more angiograms of the plurality of angiograms ($G_1$ to $G_M$) at least part of which has been transformed by the transforming processor, based on the plurality of feature point groups ($Q_1$ to $Q_K$).

The ophthalmological device 1 of the present embodiment configured in this way is capable of constructing an angiogram covering a wide area of the eye fundus (that is, a panoramic angiogram) by combining a plurality of angiograms representing different regions of the eye fundus. Thereby, the distribution and state of blood vessels can be rendered over the wide area of the eye fundus.

In the present embodiment, the transforming processor (the image transforming processor 43) may be configured to transform at least one of the first angiogram and the second angiogram, of the plurality of angiograms ($G_1$ to $G_M$), that include feature points belonging to a predetermined number or more of common feature point groups so as to match the positions of the feature points in the first angiogram and the positions of the feature points in the second angiogram. That is, the transforming processor (the image transforming processor 43) may apply a coordinate transformation to at least one of the first and second angiograms on the basis of the positions of the feature points in the first angiogram and the positions of the feature points in the second angiogram.

According to such a configuration, transformation of and registration between the first angiogram and the second angiogram can be performed with high precision and high accuracy, which makes it possible to construct a panoramic angiogram with high precision and high accuracy.

The transforming processor (the image transforming processor 43) may be configured to, if both the first angiogram and the second angiogram include feature points belonging to eight or more common feature point groups, transform at least one of the first angiogram and the second angiogram by performing a homography transformation based on eight or more feature points included in the first angiogram and eight or more feature points included in the second angiogram.

According to such a configuration, in addition to the rotation, translation, and scaling (enlargement and reduction) of the angiogram, the scaling ratio (enlargement ratio and reduction ratio) can be adjusted for each coordinate position. Thereby, highly precise and highly accurate angiogram transformation can be achieved.

the transforming processor (the image transforming processor 43) may be configured to, If both the first angiogram and the second angiogram include feature points belonging to seven or less common feature point groups, perform a coordinate transformation different from the homography transformation based on seven or less feature points included in the first angiogram and seven or less feature points included in the second angiogram.

According to such a configuration, even if the number of same feature points required for applying the homography transformation has not been obtained, the angiograms can be transformed by applying another coordinate transformation.

In some examples, the transforming processor (the image transforming processor 43) may be configured to, if both the first angiogram and the second angiogram include feature points belonging to six or more (and also seven or less) common feature point groups, perform an affine transformation based on six or more (and also seven or less) feature points included in the first angiogram and six or more (and also seven or less) feature points included in the second angiogram, or perform a Helmert transformation based on four or more (and also seven or less) feature points included in the first angiogram and four or more (and also seven or less) feature points included in the second angiogram.

In some other examples, the transforming processor (the image transforming processor 43) may be configured to, if both the first angiogram and the second angiogram include feature points belonging to four or more (and also seven or less) common feature point groups, perform a Helmert transformation based on four or more (and also seven or less) feature points included in the first angiogram and four or more (and also seven or less) feature points included in the second angiogram.

In the present embodiment, the transforming processor (the image transforming processor 43) may be configured to perform a transformation of the second angiogram on the basis of the first angiogram at least once and a transformation of the first angiogram on the basis of the second angiogram at least once.

According to such a configuration, a transformation of and registration between the first angiogram and the second angiogram can be performed with high precision and high accuracy. This leads to constructing a panoramic angiogram with high precision and high accuracy possible.

In the present embodiment, the composing processor (the image composing processor 44) may be configured to compose the two or more angiograms by projecting the two or more angiograms onto a predetermined cylindrical surface or a predetermined spherical surface.

According to such a configuration, a panoramic angiogram in accordance with the shape of the eye fundus can be constructed.

<Second Embodiment>

The ophthalmological device according to the second embodiment will be described. Similar to the ophthalmological device 1 of the first embodiment, the ophthalmological device according to the present embodiment includes the controller 10, the memory 20, the data input and output (I/O) device 30, the data processor 40, and the operation device 50 (see FIG. 1).

Figure 6:
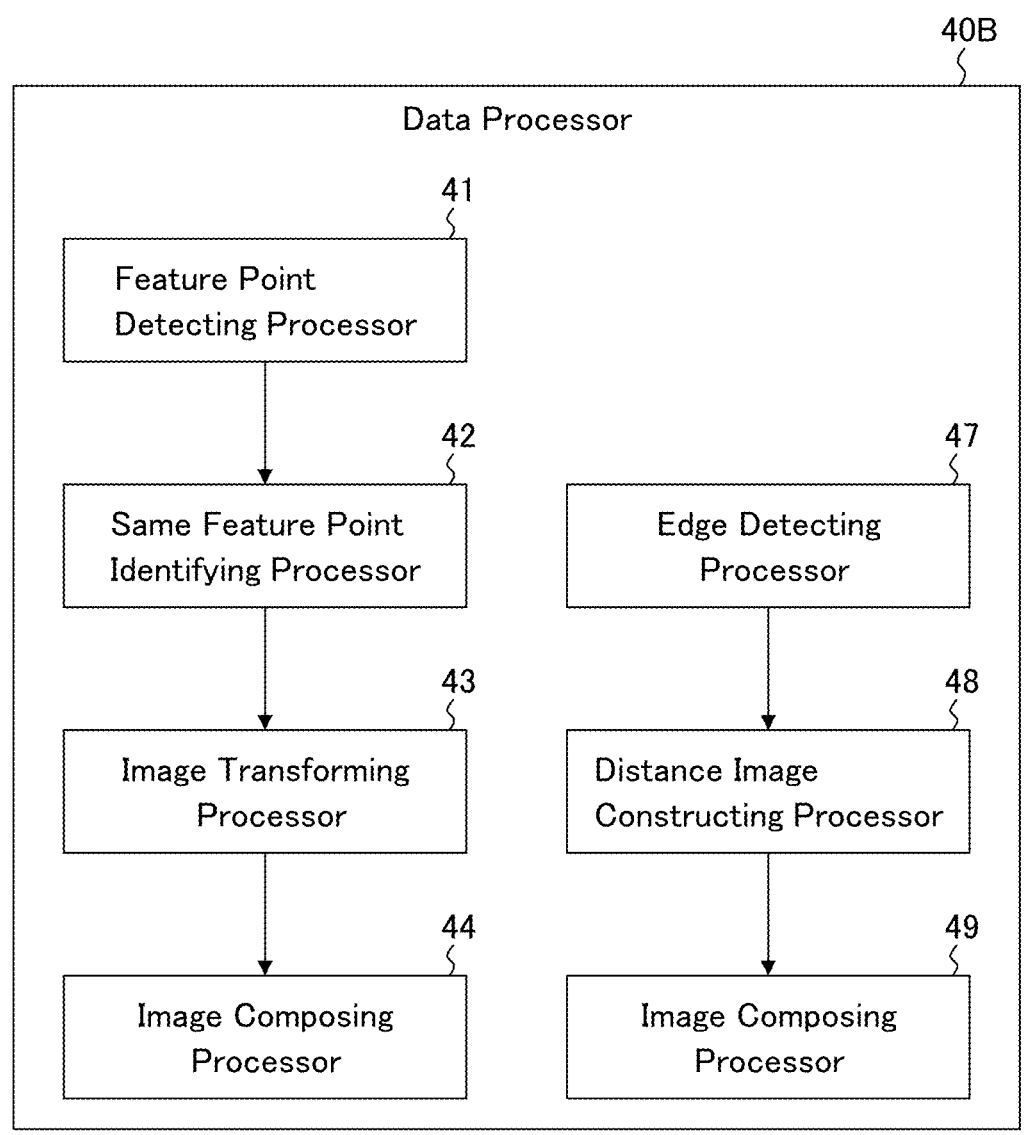
FIG. 6 is a schematic diagram illustrating an example of the configuration of the ophthalmological device according to the exemplary embodiment.

In the present embodiment, the data processor 40 is configured differently from that of the first embodiment. FIG. 6 shows a configuration example of the data processor 40 of the present embodiment. The data processor 40B shown in FIG. 6 includes the edge detecting processor 47, the distance image constructing processor 48, and the image composing processor 49, in addition to the feature point detecting processor 41, the same feature point identifying processor 42, the image transforming processor 43, and the image composing processor 44 as in the data processor 40A shown in FIG. 2.

In the event that a process performed by any of the feature point detecting processor 41, the same feature point identifying processor 42, the image transforming processor 43, and the image composing processor 44 has failed, the controller 10 changes the processing mode of the data processor 40B for panoramic angiogram construction to a processing mode for activating the edge detecting processor 47, the distance image constructing processor 48, and the image composing processor 49.

(Edge Detecting Processor 47)

Figure 7A:
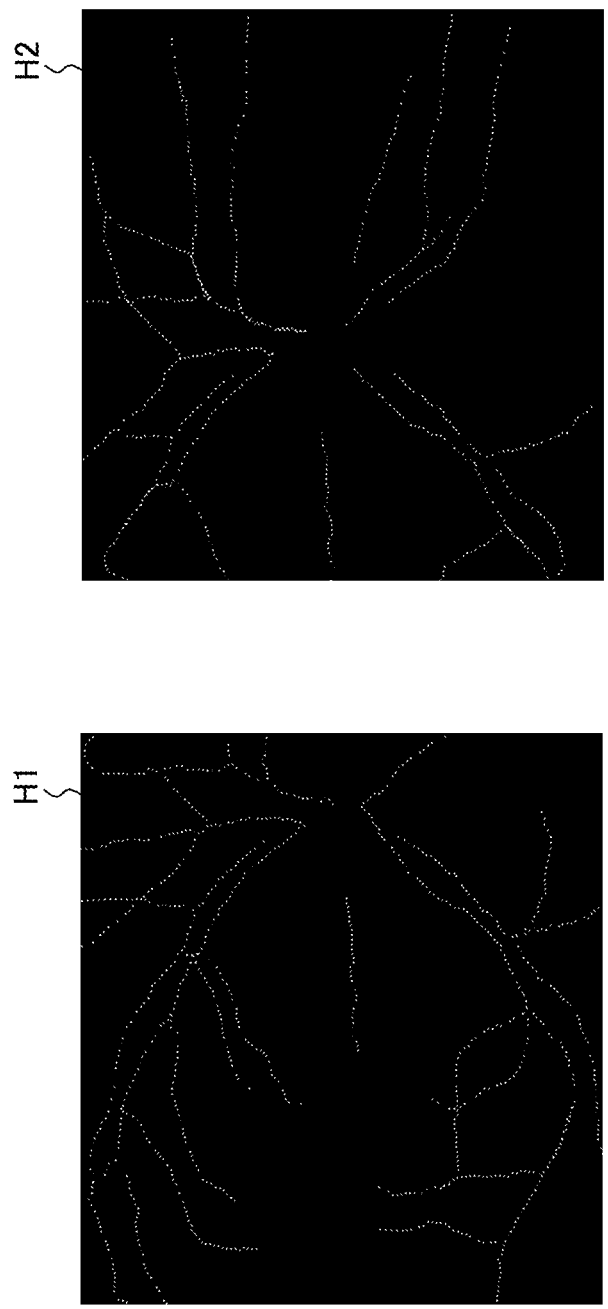
FIG. 7A is a schematic diagram for describing an example of the operation of the ophthalmological device according to the exemplary embodiment.

The edge detecting processor 47 is configured to construct a plurality of edge images by applying an edge detection to each of the plurality of angiograms ($G_1$ to $G_M$). The edge detection may be performed using any known edge detection technique. FIG. 7A shows the exemplary edge images H1 and H2 constructed by the edge detecting processor 47.

(Distance Image Constructing Processor 48)

The distance image constructing processor 48 is configured to construct a plurality of distance images by applying a Hausdorff transformation to the edge images constructed by the edge detecting processor 47. A distance image means an image in which distance information is reflected in pixel values.

In the present example, a value relating to the distance from a pixel of the edge image to the detected edge is assigned to the pixel. More specifically, for each pixel in the edge image, the distance image constructing processor 48 is configured to identify the point on the edge constructed by the edge detecting processor 47 that is closest to a concerned pixel, calculate the distance between the identified point and the concerned pixel, and then assign a pixel value corresponding to the calculated distance to the concerned pixel.

FIG. 7B shows the distance image D1 and the distance image D2 constructed from the edge image H1 and the edge image H2 shown in FIG. 7A, respectively.

(Image Composing Processor 49)

The image composing processor 49 is configured to compose two or more angiograms among the plurality of angiograms by applying position matching (registration) to the distance images constructed by the distance image constructing processor 48. Thereby, a panoramic angiogram is obtained.

In the case of considering the first distance image based on the first angiogram and the second distance image based on the second angiogram, the image composing processor 49, for example, determines the difference between the overlapping regions of the first distance image and the second distance image while changing the relative position between the first distance image and the second distance image, and then identifies a relative position between the first distance image and the second distance image so that the amount of the difference becomes minimum. In such a way, the relative position between the first angiogram and the second angiogram respectively corresponding to the first distance image and the second distance image is determined.

The image composing processor 49 composes two or more angiograms among the angiograms according to the relative positional relationship determined in this manner.

Figure 8:
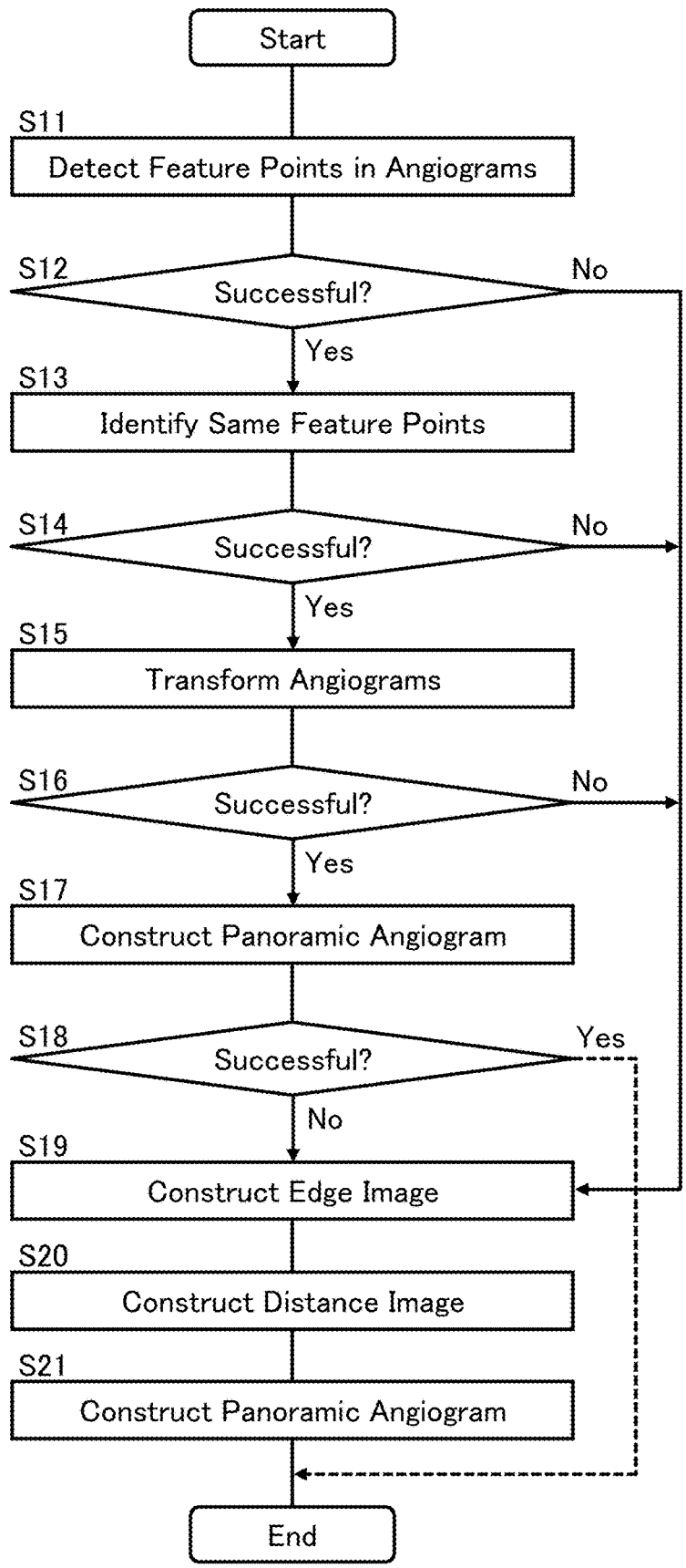
FIG. 8 is a flowchart illustrating an example of the operation of the ophthalmological device according to the exemplary embodiment.

FIG. 8 shows an example of the operation flow of the ophthalmological device of the present embodiment. The steps S11, S13, S15, and S17 are executed in the same manner as the steps S3, S4, S5, and S6 of FIG. 3 of the first embodiment, respectively.

In the step S12, the determination process whether or not the feature point detection in the step S11 has been successful is performed. The determination process is executed by the controller 10 based on a predetermined determination criterion, for example. Examples of the determination criterion include the followings: no feature point is detected from an angiogram; the number of feature points detected from an angiogram is less than a predetermined threshold; and the number of feature points detected from all the angiograms is less than a predetermined threshold.

In the step S14, the determination whether or not the same feature point identification in the step S13 has been successful is performed. The determination process is executed by the controller 10 based on a predetermined determination criterion, for example. Examples of the determination criterion include the followings: no same feature point is identified; and that the number of the identified feature points is less than a predetermined threshold.

In the step S16, the determination whether or not the angiogram transformation (coordinate transformation of angiograms) in the step S15 has been successful is performed. The determination process is executed by the controller 10 based on a predetermined determination criterion, for example. An example of the determination criterion is that a coordinate transformation matrix cannot be calculated.

In the step S18, the determination whether or not the panoramic angiogram construction (angiogram composition) in the step S17 has been successful is performed. The determination process is executed by the controller 10 based on a predetermined determination criterion, for example. Examples of the determination criterion include the followings: the number of composed angiograms is less than a predetermined threshold; and the resulting panoramic angiogram does not include an image of a predetermined tissue of the eye fundus such as the optic nerve head, the macula, of a lesion.

In the event that all the determination processes in the steps S12, S14, S16, and S18 are "successful (Yes)", the operation flow of the present example becomes the same as that in FIG. 3 of the first embodiment.

On the other hand, in the event that any one or more of the determinations in the steps S12, S14, S16, and S18 are "unsuccessful (No)", the operation flow of the present example proceeds to the step S19.

In the step S19, the edge detecting processor 47 constructs a plurality of edge images from the angiograms. Subsequently, in the step S20, the distance image constructing processor 48 constructs a plurality of distance images by applying a Hausdorff transformation to the edge images constructed in the step S19. Furthermore, in the step S21, the image composing processor 49 composes two or more angiograms among the angiograms by applying registration to the distance images constructed in the step S20. Thereby, a panoramic angiogram is constructed.

According to the embodiment as described above, a panoramic angiogram can still be constructed, even though any of the processes in the first embodiment has failed, by changing to another processing mode.

This another processing mode is executed to construct distance images from edge images of angiograms. Since such distance images thus constructed contain more information (i.e., distance information assigned to each pixel) than the angiograms or the edge images, registration between angiograms can be carried out in a preferable manner.

<Third Embodiment>

Figure 9:
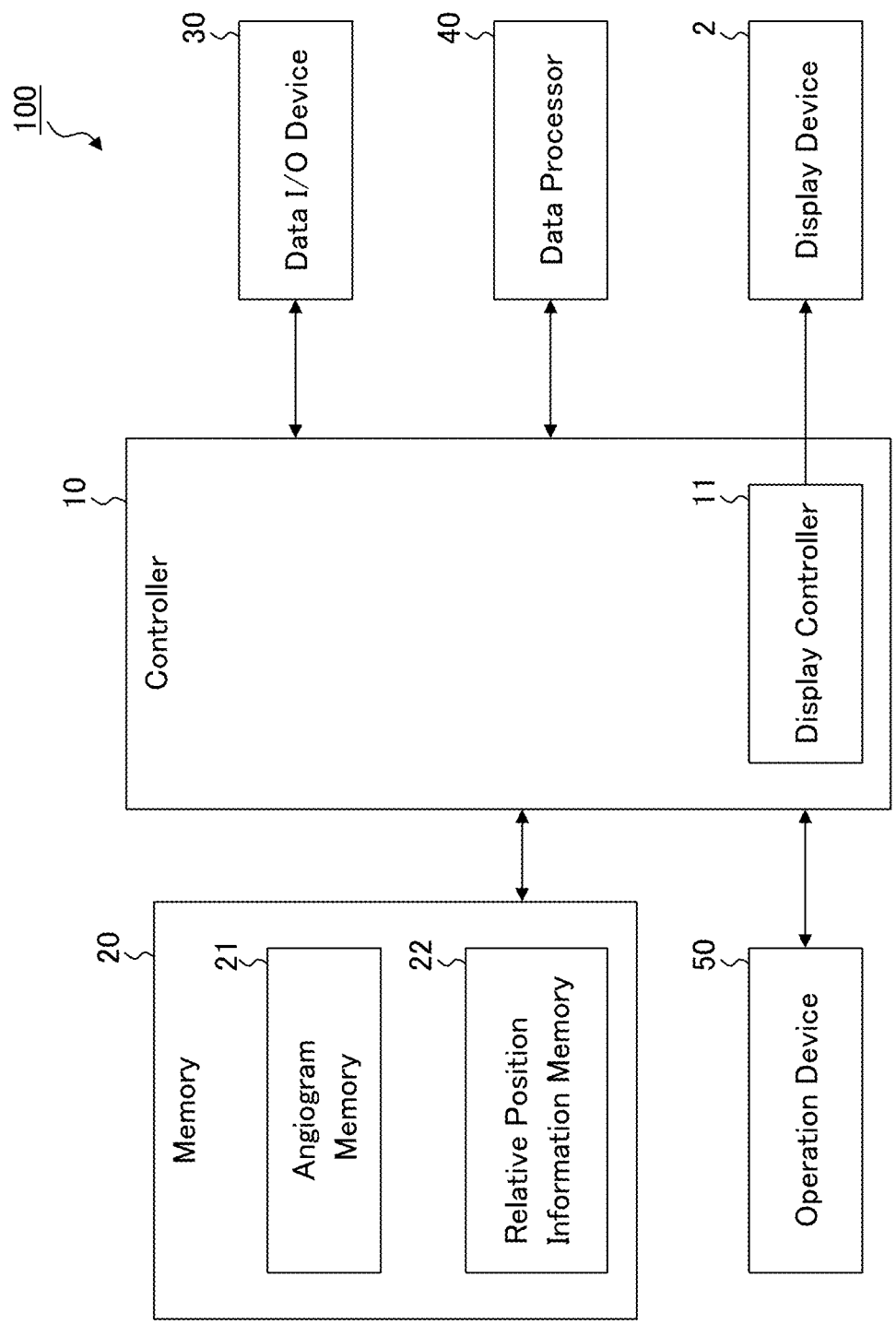
FIG. 9 is a schematic diagram illustrating an example of the configuration of the ophthalmological device according to the exemplary embodiment.

The ophthalmological device according to the third embodiment will be described. FIG. 9 shows a configuration example of the ophthalmological device according to the present embodiment. Similar to the ophthalmological device 1 of the first embodiment, the exemplary ophthalmological device 100 includes the controller 10, the memory 20, the data input and output (I/O) device 30, the data processor 40, and the operation device 50 (see FIG. 1). The data processor 40 may have the configuration shown in FIG. 2 or FIG. 6.

In the present embodiment, the memory 20 includes the relative position information memory 22. The relative position information memory 22 stores relative position information representing the relative positions between the plurality of angiograms stored in the angiogram memory 21.

The relative position information includes, for example, information indicating fixation positions when OCT scans for constructing the angiograms have been applied to the subject's eye. In some other examples, the relative position information includes information indicating a tissue(s) of the eye fundus (e.g., optic nerve head, macula) depicted in the angiograms. In still other examples, the relative position information includes information indicating the positions (locations) of the angiograms in a fundus image of the subject's eye (e.g., a fundus image representing a wider area than the angiograms) obtained using, for example, a fundus camera (retinal camera) or a scanning laser ophthalmoscope (SLO).

The form of relative position information is arbitrary. For example, the relative position information may include a table data in which position information for each of the angiograms is recorded. Alternatively, the relative position information may be attached to the angiograms (image data). For example, the relative position information of the angiograms can be recorded in the DICOM tag information of the angiograms.

Note that DICOM is an abbreviation for "Digital Imaging and Communications in Medicine", which is the standard that defines the formats and communication protocols of medical images. A DICOM tag is tag information provided in the DICOM file.

In the present embodiment, at least one of the feature point detecting processor 41, the same feature point identifying processor 42, the image transforming processor 43, and the image composing processor 44 performs processing based on the relative position information stored in the relative position information memory 22.

The feature point detecting processor 41 may be configured to limit a search area for feature points by referring to the relative position information, for example. Typically, the feature point detecting processor 41 may be configured to identify or estimate overlapping regions between angiograms from the relative positions of the angiograms represented in the relative position information. Then, the feature point detecting processor 41 may detect feature points only from the identified or estimated overlapping regions. As a result, resources required for feature point search can be reduced and time required for the search can be shortened.

Similarly, the same feature point identifying processor 42 may be configured to limit the search area for the same feature points by referring to the relative position information. Further, by referring to the relative position information, the same feature point identifying processor 42 may identify or deduce an angiogram group that may include the same feature points. According to such processing, resources required for searching for the same feature points can be reduced and the search time can be shortened.

The image transforming processor 43 may be configured to transform at least one of angiograms by limiting to only their overlapping regions by referring to the relative position information, for example. With this, resources required for the image transformation processing can be reduced and the processing time can be shortened.

The image composing processor 44 may be configured to determine or estimate a rough arrangement of angiograms by referring to the relative position information, for example. As a result, resources required for the image composition processing can be reduced and the processing time can be shortened.

<Fourth Embodiment>

The ophthalmological device according to the fourth embodiment will be described. The ophthalmological device according to the fourth embodiment has the function of constructing angiograms by applying OCT angiography to the fundus of the subject's eye. Therefore, the ophthalmological device according to the fourth embodiment is an OCT apparatus that includes at least a computer (including hardware such as a processor, and software) and an OCT scanner while the ophthalmological device according to any of the first to third embodiments includes at least such a computer.

Figure 10:
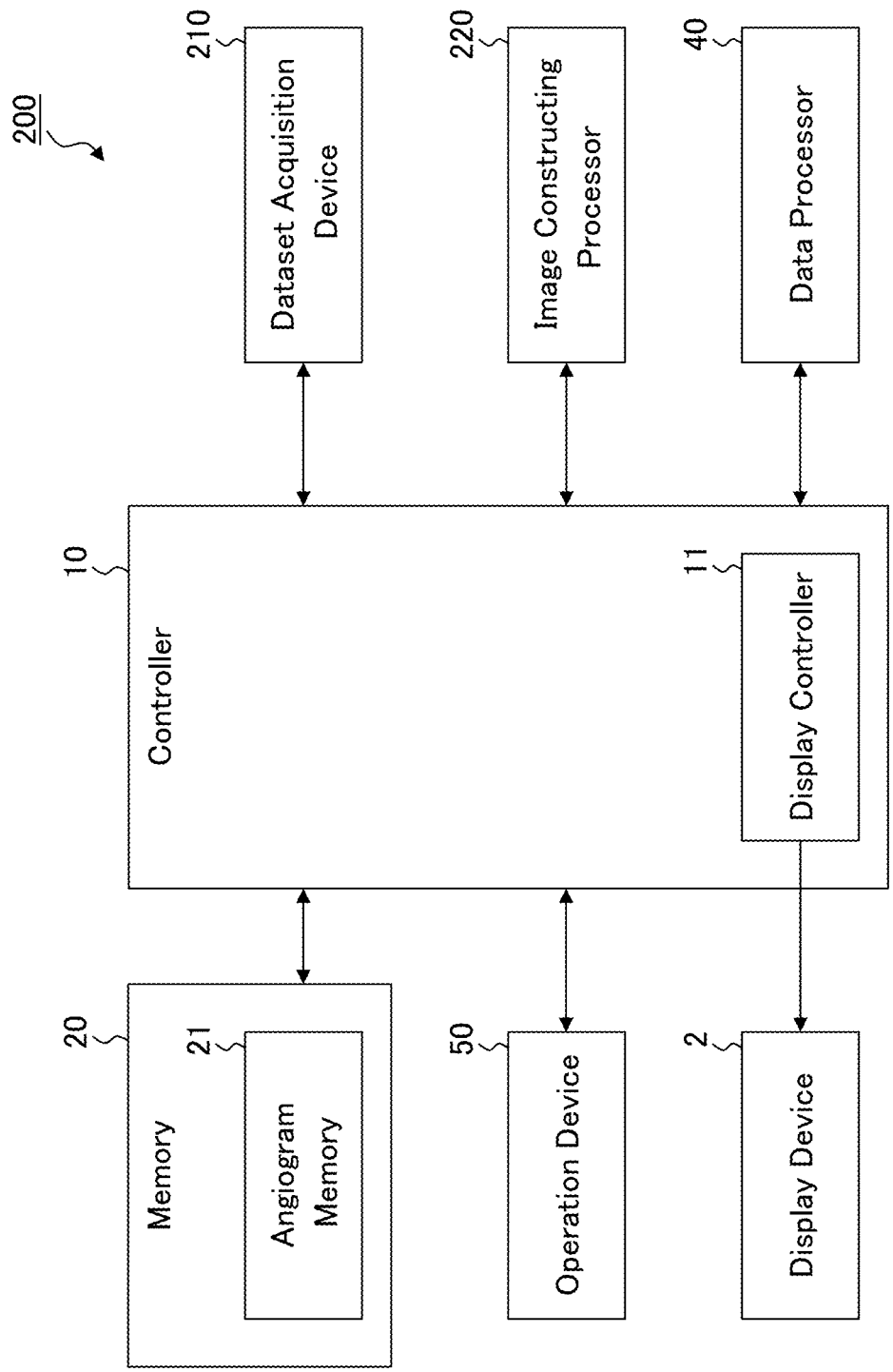
FIG. 10 is a schematic diagram illustrating an example of the configuration of the ophthalmological device according to the exemplary embodiment.

FIG. 10 shows an example of the ophthalmological device according to the fourth embodiment. As in the first to third embodiments, the ophthalmological device 200 includes the controller 10, the memory 20, the data processor 40, and the operation device 50 (see FIG. 1). In addition to these, the ophthalmological device 200 includes the dataset acquisition device 210 and the image constructing processor 220. The data processor 40 may be either the data processor 40A or 40B described above. In addition, the ophthalmological device 200 may further include the data input and output (I/O) device 30 as in the first to third embodiments.

The dataset acquisition device 210 includes a configuration (elements) for applying OCT scanning to the eye fundus, such as an optical system, a drive system, a control system, and a data processing system. Each of the systems may have a known configuration. The dataset acquisition device 210 is configured to be capable of executing Fourier domain OCT, for example. The Fourier domain OCT executed by the dataset acquisition device 210 may be spectral domain OCT and/or swept source OCT.

The spectral domain OCT is an OCT technique of obtaining a data set from a sample by acquiring spectra of interference light in a space division manner using a broadband low coherence light source and a spectroscope, and by applying Fourier transform to the spectra of the interference light acquired.

The swept source OCT is an OCT technique of obtaining a data set from a sample by acquiring spectra of interference light in a time division manner using a wavelength swept light source (wavelength tunable light source) and a photodetector (e.g., a balanced photodiode), and by applying Fourier transform to the spectra of the interference light acquired.

The ophthalmological device 200 may include modalities other than OCT. Examples of such optional modalities include a fundus camera (retinal camera), a scanning laser ophthalmoscope (SLO), a slit lamp microscope, and an ophthalmological surgical microscope. Furthermore, the ophthalmological device 200 may include an apparatus used for ophthalmological treatment. One example of such a ophthalmological treatment apparatus is a laser treatment apparatus used for photocoagulation treatment or the like.

The dataset acquisition device 210 is configured to acquire a three dimensional data set by applying OCT scanning to the eye fundus. The dataset acquisition device 210 includes the following configurations: a configuration to perform optical measurements using the spectral domain OCT or the swept source OCT (e.g., an optical system, a drive system, a control system, etc.); and a configuration to construct a three dimensional data set based on the data acquired by the OCT scanning. The image data construction executed here may include known processes such as noise elimination (noise reduction), filtering, Fast Fourier Transform (FFT), and the like as in the conventional OCT techniques, for example.

The dataset acquisition device 210 is configured to apply OCT scanning to a three dimensional region of the subject's eye. The mode of the OCT scanning here is, for example, a raster scan (also referred to as a three dimensional scan). The raster scan is carried out, for example, by scanning each of a plurality of B-scan cross sections a predetermined number of times. That is, the raster scan is carried out, for example, by sequentially scanning the plurality of B-scan cross sections a predetermined number of times each.

The dataset acquisition device 210 is further configured to construct a plurality of cross sectional images (B-scan images) for each of the B-scan cross sections based on data acquired by the raster scan.

Furthermore, the dataset acquisition device 210 is further configured to construct stack data by embedding the constructed cross sectional images in a single three dimensional coordinate system. In this stack data, a predetermined number of cross sectional images are assigned to each of the B-scan cross sections. Further, volume data (i.e., voxel data) may be constructed by performing interpolation processing etc. on the stack data. In this volume data as well, a predetermined number of voxel groups are assigned to each of the locations respectively corresponding to the B-scan cross sections. Such stack data and volume data are examples of three dimensional data sets.

The three dimensional data set acquired by the dataset acquisition device 210 is sent to the image constructing processor 220. The image constructing processor 220 is configured to construct angiograms based on the three dimensional data set acquired by the dataset acquisition device 210. The angiogram construction here is executed in the same manner as in the conventional techniques.

The ophthalmological device 200 may have a function of presenting a fixation target to the subject's eye. For example, the ophthalmological device 200 may include a display device configured to display an image used as a fixation target and arranged coaxially with the optical path for OCT scanning. The controller 10 may change the fixation position by changing the display position of the image displayed by the display device. Information indicating the fixation position applied during application of OCT scanning may be associated with angiograms constructed based on the OCT scanning.

The present example may be configured to construct a plurality of angiograms corresponding to a plurality of different regions of the eye fundus, by performing repetitive (iterative) OCT angiography on the eye fundus while sequentially switching and applying a plurality of fixation positions to the subject's eye. The plurality of fixation positions may be designed so that, for example, a plurality of angiograms acquired is arranged in a predetermined layout, and the angiograms have overlapping regions.

The angiograms acquired in this way are stored in the angiogram memory 21 by the controller 10. To the angiograms, the ophthalmological device 200 applies any of the processes described in any of the first to third embodiments described above, for example. Thereby, a panoramic angiogram that is a composite image (merged image) of at least two of the angiograms is constructed.

The configurations, embodiments, and aspects described above are merely examples in order to implement the present invention, and any modifications (e.g., omissions, replacements, substitutions, additions) can be made within the scope of the gist of the present invention.

Any two or more of the first to fourth embodiments may be combined.

What we claim is:

1. An ophthalmological device comprising:
a memory that stores a plurality of angiograms acquired by applying optical coherence tomography to a fundus of a subject's eye;
processing circuitry configured to detect a feature point from each of the plurality of angiograms;
the processing circuitry further configured to identify a plurality of feature point groups from among a plurality of feature points detected from the plurality of angiograms by the processing circuitry, each of the plurality of feature point groups corresponding to a same site of the fundus;
the processing circuitry further configured to transform at least part of the plurality of angiograms based on the plurality of feature point groups identified by the processing circuitry; and
the processing circuitry further configured to compose two or more angiograms of the plurality of angiograms at least part of which has been transformed by the processing circuitry, based on the plurality of feature point groups, wherein
the processing circuitry transforms at least one of a first angiogram and a second angiogram of the plurality of angiograms that include feature points belonging to a predetermined number or more of common feature point groups, to perform position matching between a feature point included in the first angiogram and a feature point included in the second angiogram,
wherein in the event that both the first angiogram and the second angiogram include feature points belonging to any of four to seven common feature point groups, the processing circuitry performs a Helmert transformation based on any of four to seven feature points included in the first angiogram and any of four to seven feature points included in the second angiogram.

2. The ophthalmological device of claim 1, wherein the processing circuitry performs a transformation of the second angiogram on the basis of the first angiogram at least once and a transformation of the first angiogram on the basis of the second angiogram at least once.

3. The ophthalmological device of claim 1, wherein the processing circuitry composes the two or more angiograms by projecting the two or more angiograms onto a predetermined cylindrical surface.

4. The ophthalmological device of claim 1, wherein the processing circuitry composes the two or more angiograms by projecting the two or more angiograms onto a predetermined spherical surface.

5. The ophthalmological device of claim 1, wherein
the memory stores relative position information that represents a relative position between the plurality of angiograms, and
the processing circuitry performs a process based on the relative position information.

6. The ophthalmological device of claim 1, further comprising:
an optical coherence tomography scanner configured to acquire a three dimensional data set by applying optical coherence tomography to the fundus; and
the processing circuitry further configured to construct an angiogram based on the three dimensional data set acquired by the optical coherence tomography scanner,
wherein the memory stores the angiogram constructed by the processing circuitry.

7. An ophthalmological device comprising:
a memory that stores a plurality of angiograms acquired by applying optical coherence tomography to a fundus of a subject's eye;
processing circuitry configured to detect a feature point from each of the plurality of angiograms;
the processing circuitry further configured to identify a plurality of feature point groups from among a plurality of feature points detected from the plurality of angiograms by the processing circuitry, each of the plurality of feature point groups corresponding to a same site of the fundus;

the processing circuitry further configured to transform at least part of the plurality of angiograms based on the plurality of feature point groups identified by the processing circuitry;

the processing circuitry further configured to compose two or more angiograms of the plurality of angiograms at least part of which has been transformed by the processing circuitry, based on the plurality of feature point groups;

the processing circuitry further configured to construct a plurality of edge images by applying an edge detection to each of the plurality of angiograms in the event that a process performed by the processing circuitry has failed; and the processing circuitry further configured to construct a plurality of distance images by applying a Hausdorff transformation to the plurality of edge images, wherein the processing circuitry is configured to compose the two or more angiograms of the plurality of angiograms by applying registration to the plurality of distance images.

8. A method of processing an ophthalmological image, the method comprising:

storing a plurality of angiograms acquired by applying optical coherence tomography to a fundus of a subject's eye;

detecting a feature point from each of the plurality of angiograms;

identifying a plurality of feature point groups from among a plurality of feature points detected from the plurality of angiograms, each of the plurality of feature point groups corresponding to a same site of the fundus;

transforming at least part of the plurality of angiograms based on the plurality of feature point groups identified; and composing two or more angiograms of the plurality of angiograms at least part of which has been transformed, based on the plurality of feature point groups, wherein the transforming is performed by transforming at least one of a first angiogram and a second angiogram of the plurality of angiograms that include feature points belonging to a predetermined number or more of common feature point groups, to perform position matching between a feature point included in the first angiogram and a feature point included in the second angiogram, wherein in the event that both the first angiogram and the second angiogram include feature points belonging to any of four to seven common feature point groups, the transforming is performed by a Helmert transformation based on any of four to seven feature points included in the first angiogram and any of four to seven feature points included in the second angiogram.

9. A computer-readable non-transitory storage medium storing a program configured to cause a computer to perform the method of processing an ophthalmological image of claim 8.

10. A method of processing an ophthalmological image, the method comprising:

storing a plurality of angiograms acquired by applying optical coherence tomography to a fundus of a subject's eye;

detecting a feature point from each of the plurality of angiograms;

identifying a plurality of feature point groups from among a plurality of feature points detected from the plurality of angiograms, each of the plurality of feature point groups corresponding to a same site of the fundus;

transforming at least part of the plurality of angiograms based on the plurality of feature point groups identified;

composing two or more angiograms of the plurality of angiograms at least part of which has been transformed, based on the plurality of feature point groups;

constructing a plurality of edge images by applying an edge detection to each of the plurality of angiograms in the event that any of the detecting, the identifying, the transforming, and the composing has failed;

constructing a plurality of distance images by applying a Hausdorff transformation to the plurality of edge images; and composing two or more angiograms of the plurality of angiograms by applying registration to the plurality of distance images.

11. A computer-readable non-transitory storage medium storing a program configured to cause a computer to perform the method of processing an ophthalmological image of claim 10.

* * * * *